(12) United States Patent
Lampropoulos et al.

(10) Patent No.: US 11,160,629 B2
(45) Date of Patent: Nov. 2, 2021

(54) MEDICAL DEVICE DISPENSER AND METHOD OF USE

(71) Applicant: Merit Medical Systems, Inc., South Jordan, UT (US)

(72) Inventors: Fred Lampropoulos, Salt Lake City, UT (US); Michael O. Daily, Salt Lake City, UT (US); Jim Mottola, West Jordan, UT (US); Frank P. Gazzano, Mesa, AZ (US); Richard P. Jenkins, Bluffdale, UT (US); Mahender Avula, Sandy, UT (US); Kenneth Sykes, Bluffdale, UT (US); Christopher Cindrich, Draper, UT (US); Gregory R. McArthur, Sandy, UT (US); Diana N. Caldwell, West Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 58 days.

(21) Appl. No.: 16/126,646

(22) Filed: Sep. 10, 2018

(65) Prior Publication Data
US 2019/0076205 A1    Mar. 14, 2019

Related U.S. Application Data

(60) Provisional application No. 62/557,489, filed on Sep. 12, 2017, provisional application No. 62/613,661, filed on Jan. 4, 2018.

(51) Int. Cl.
*A61B 50/30* (2016.01)
*A61M 5/32* (2006.01)
*A61B 50/20* (2016.01)
*A61J 1/00* (2006.01)
*A61B 50/22* (2016.01)

(52) U.S. Cl.
CPC .............. *A61B 50/30* (2016.02); *A61B 50/20* (2016.02); *A61M 5/3202* (2013.01); *A61B 50/22* (2016.02); *A61B 2050/3011* (2016.02); *A61B 2050/314* (2016.02); *A61J 1/00* (2013.01)

(58) Field of Classification Search
CPC ...................................................... A61B 50/30
See application file for complete search history.

(56) References Cited

U.S. PATENT DOCUMENTS

| | | | |
|---|---|---|---|
| 4,283,000 A | 8/1981 | White | |
| 4,308,974 A * | 1/1982 | Jones | A61F 15/001 |
| | | | 221/196 |

(Continued)

FOREIGN PATENT DOCUMENTS

KR     1020150086971     7/2015

OTHER PUBLICATIONS

International Search Report and Written Opinion dated Mar. 15, 2019 for PCT/US2018/050269.
European Search Report dated May 12, 2021 for EP18856823.2.

*Primary Examiner* — Gene O Crawford
*Assistant Examiner* — Ayodeji T Ojofeitimi
(74) *Attorney, Agent, or Firm* — Stoel Rives LLP

(57) ABSTRACT

Medical device dispensers along with related systems and methods are disclosed herein. In some embodiments dispenses within the scope of this disclosure may be configured to couple another structure such as an IV pole. Additionally, dispensers within the scope of this disclosure may be configured with locking or otherwise tamper resistant elements.

20 Claims, 21 Drawing Sheets

(56) References Cited

U.S. PATENT DOCUMENTS

| | | | |
|---|---|---|---|
| 5,954,228 A | | 9/1999 | Minnette |
| 5,988,433 A | * | 11/1999 | Crum .................. A63B 47/002 |
| | | | 221/309 |
| 6,763,971 B1 | * | 7/2004 | Tong ...................... G07F 11/44 |
| | | | 221/151 |
| 6,948,634 B2 | * | 9/2005 | Evans ................ B65D 43/021 |
| | | | 221/202 |
| 7,017,780 B2 | * | 3/2006 | Renaud ............. B65D 83/0409 |
| | | | 221/263 |
| 8,186,543 B1 | * | 5/2012 | Hopwood .............. A47G 21/12 |
| | | | 221/192 |
| 9,775,746 B2 | * | 10/2017 | Pellerin .................. A61F 11/08 |
| 2002/0040912 A1 | | 4/2002 | McHugh |
| 2003/0173374 A1 | * | 9/2003 | Schwarzli ................ G07F 9/10 |
| | | | 221/132 |
| 2003/0201277 A1 | * | 10/2003 | Baker ...................... A47F 1/10 |
| | | | 221/266 |
| 2005/0077311 A1 | * | 4/2005 | Chang .................... G07F 11/54 |
| | | | 221/121 |
| 2008/0116219 A1 | * | 5/2008 | Lawrence ............... G07F 11/54 |
| | | | 221/265 |
| 2008/0308441 A1 | | 12/2008 | Erickson et al. |
| 2009/0294604 A1 | * | 12/2009 | Sunderland ......... A61M 5/1415 |
| | | | 248/124.1 |
| 2011/0017213 A1 | | 1/2011 | Vadney |
| 2014/0117036 A1 | * | 5/2014 | Smith ...................... A47F 1/10 |
| | | | 221/1 |
| 2015/0179018 A1 | * | 6/2015 | Rudek .................. A61F 15/001 |
| | | | 221/186 |
| 2016/0096675 A1 | * | 4/2016 | Dai .................... B65D 83/0083 |
| | | | 221/277 |
| 2017/0087025 A1 | | 3/2017 | Pellerin et al. |

\* cited by examiner

MEDICAL DEVICE DISPENSER AND METHOD OF USE

RELATED APPLICATIONS

This application claims priority to U.S. Provisional Application No. 62/557,489, filed on Sep. 12, 2017 and titled "Medical Device Dispenser and Method of Use," and U.S. Provisional Application No. 62/613,661, filed on Jan. 4, 2018 and titled, "Medical Device Dispenser and Method of Use," both of which are hereby incorporated by reference in their entireties.

TECHNICAL FIELD

This present disclosure relates to medical devices and systems for providing infection control for infusion therapy. The features relating to the methods and devices described herein can be applied to conveniently provide and safely dispense infection control infusion therapy caps and related devices.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Figure 1A:
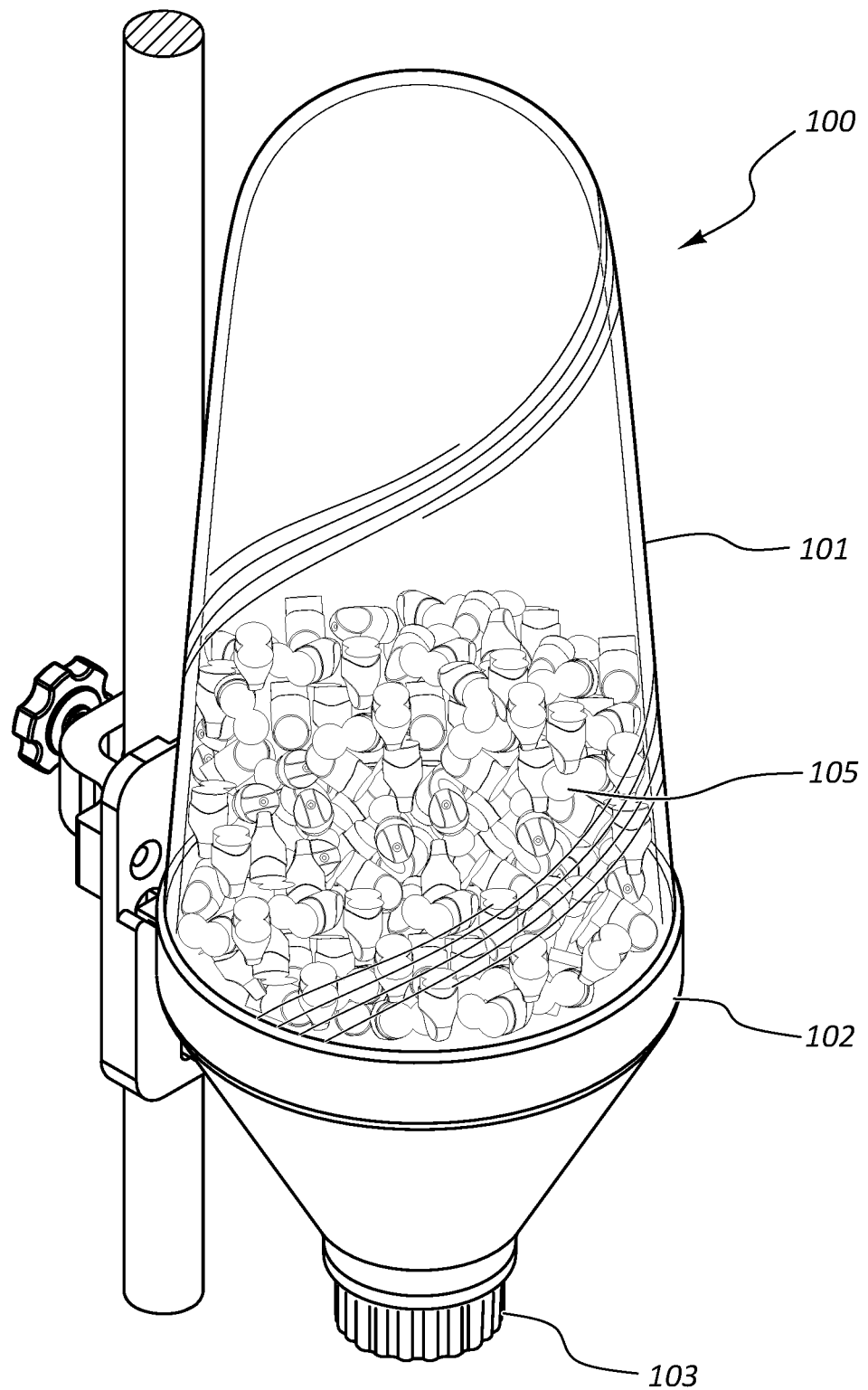
FIG. 1A is a view of a medical device dispenser.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrase "coupled to" and refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

Infusion therapy procedures are some of the most common procedures performed in a clinical care environment and the source of catheter related blood stream infections (CRBSI). CRBSIs may lead to serious morbidities, increased healthcare costs, and death. Many medical devices have been developed to reduce the risk of CRBSI to patients being treated with infusion therapy. These devices include disinfecting Luer caps configured to disinfect and maintain sterility of needleless access devices and male Luer fittings. The disinfecting caps include a body configured to couple with a needleless access device or male Luer fitting and a disinfecting agent such as alcohol. The disinfecting caps may be provided at the bedside for convenience and to support consistent use by a healthcare worker. Availability of the disinfecting caps at the bedside may also provide access to the caps to patients, especially children, leading to accidental ingestion of the caps.

FIGS. 1A-2E illustrate different views of embodiments of medical device dispensers such as cap dispensers and related components configured to dispense medical devices such as disinfecting caps in a convenient and safe manner. In certain views each medical device dispenser may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any figure or embodiment. Further, though the specific examples described herein may reference "cap dispensers" and/or "caps" the disclosure may be applied to a wide variety of medical device dispensers and medical devices. Thus, cap dispensers and caps are examples of medical device dispensers and medical devices, respectively, within the scope of this disclosure.

Figure 1B:
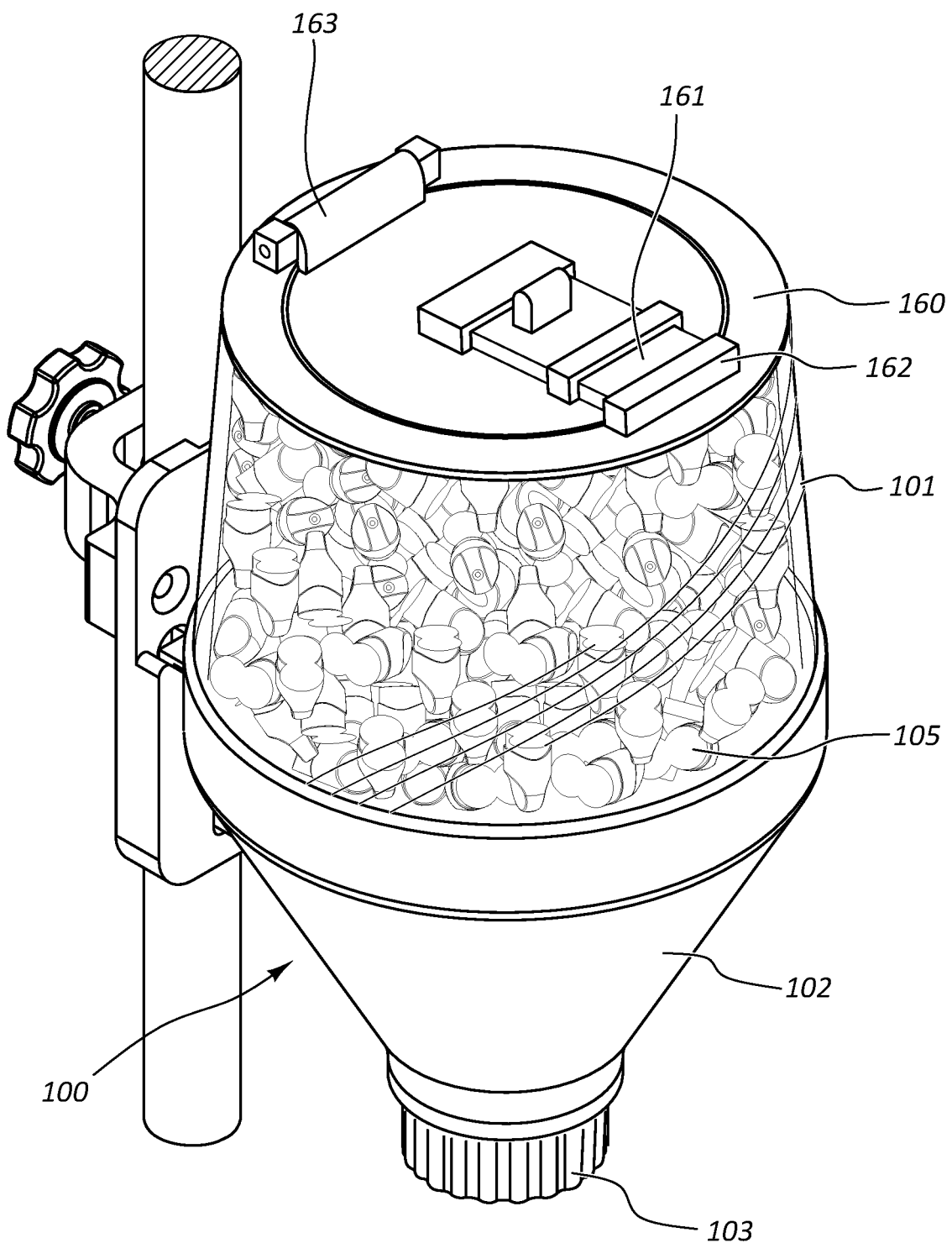
FIG. 1B is a view of the medical device dispenser with a lockable lid.
Figure 1C:
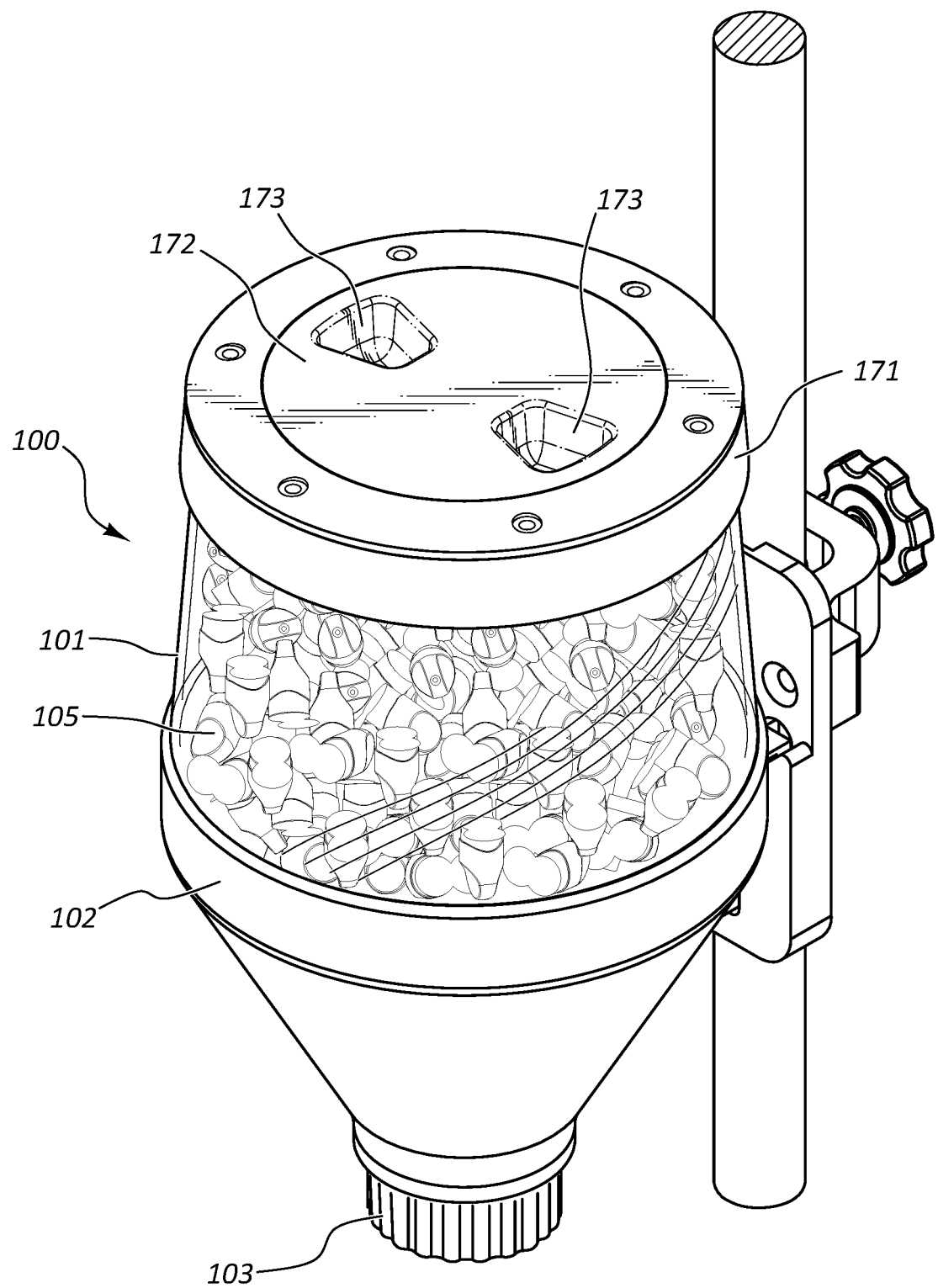
FIG. 1C is a view of the medical device dispenser with a twist open lid.
Figure 1D:
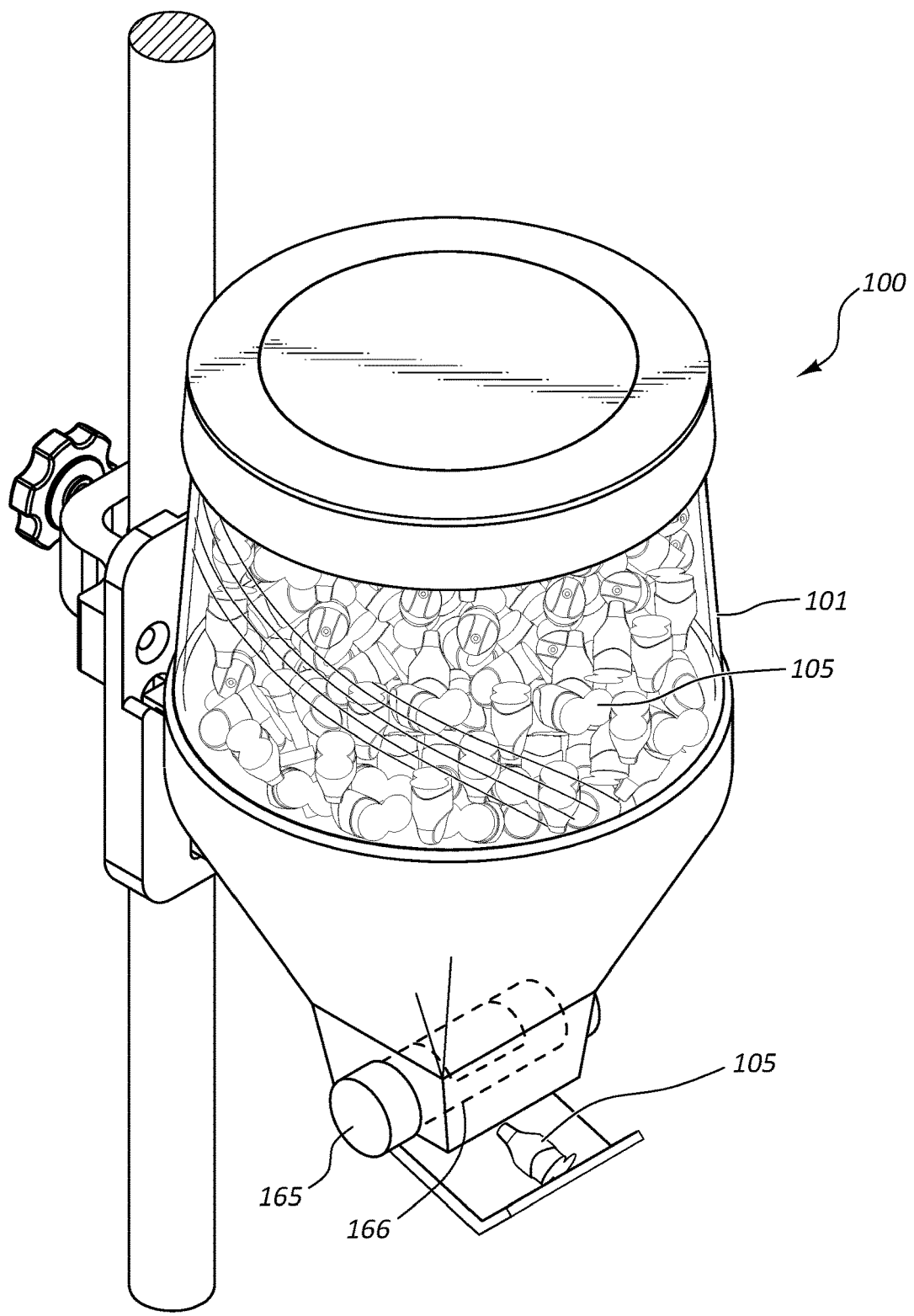
FIG. 1D is a view of the medical device dispenser having a horizontal rotary dispensing mechanism.
Figure 1E:
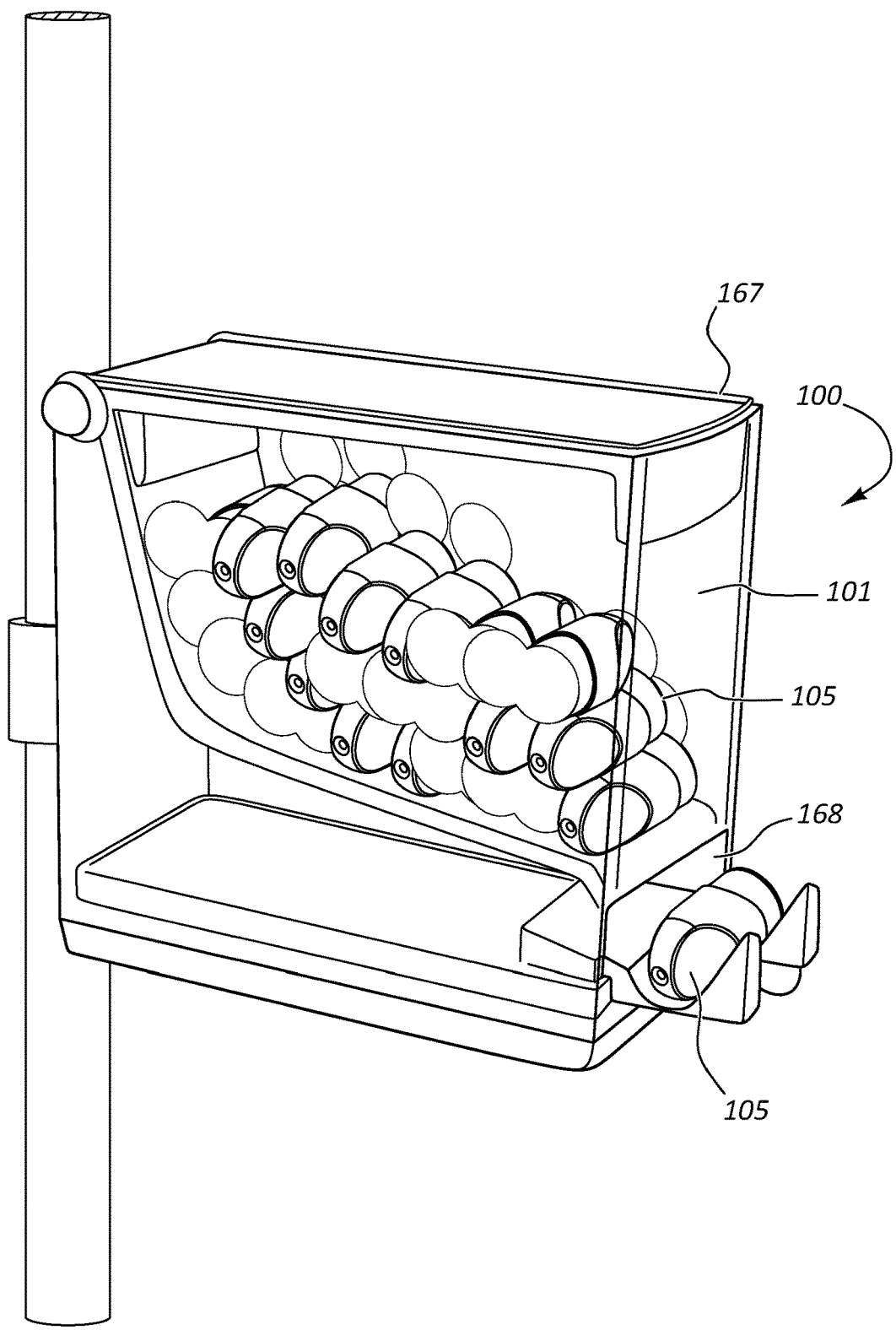
FIG. 1E is a view of the medical device dispenser having a depressible hopper dispensing mechanism.
Figure 1F:
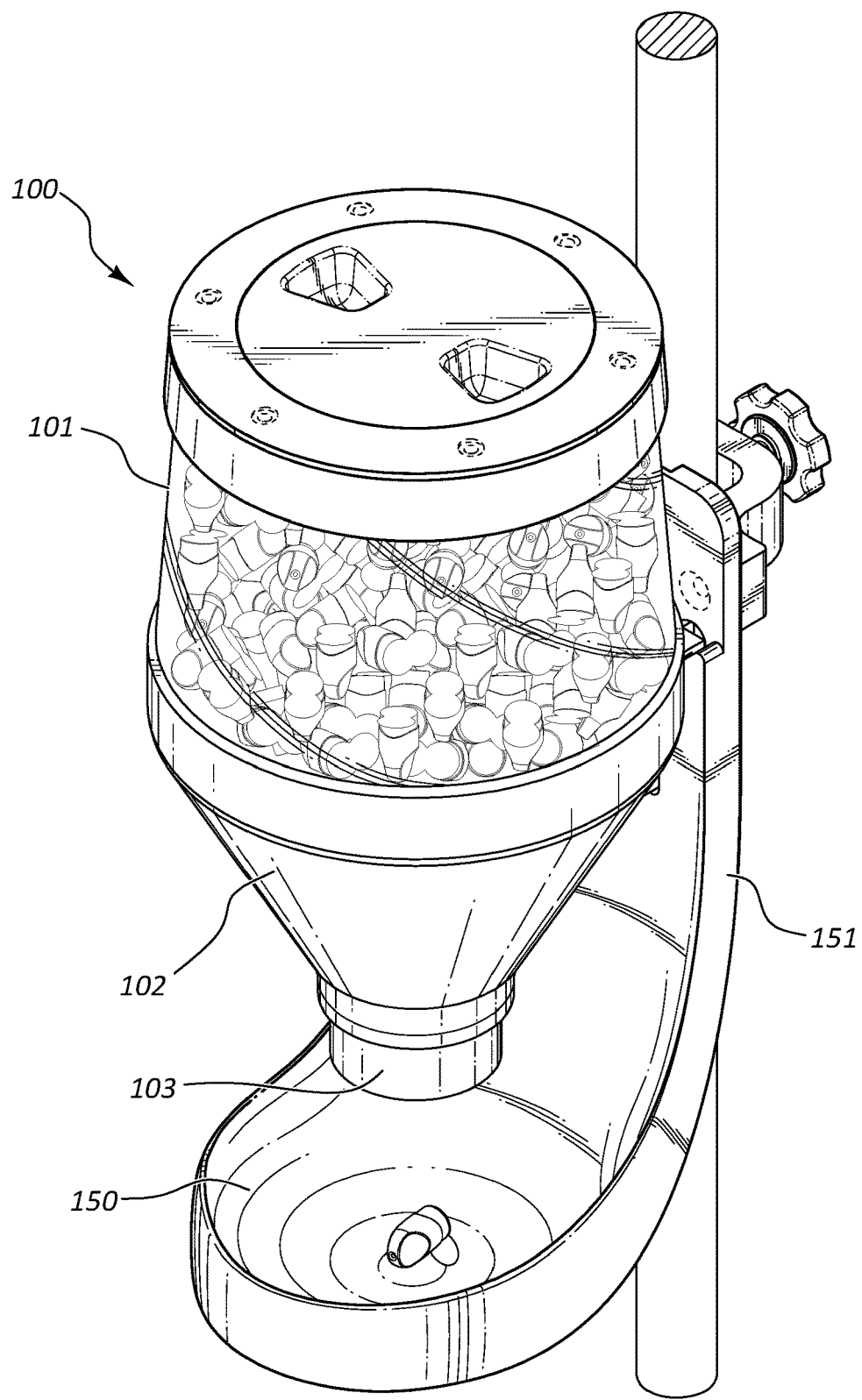
FIG. 1F is a view of the medical device dispenser with a catch tray.
Figure 1G:
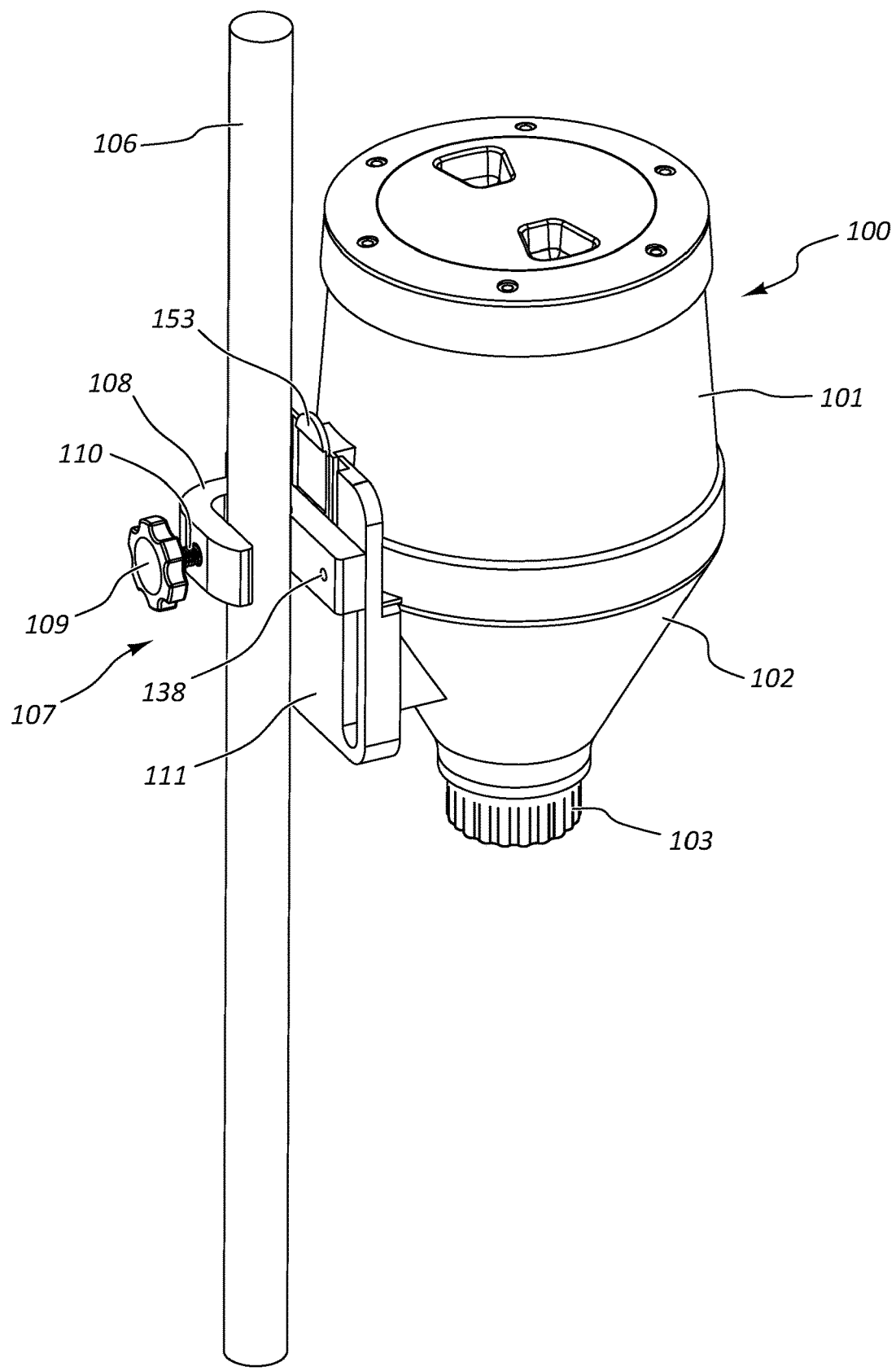
FIG. 1G is a side view of a clamp and bracket to secure the medical device dispenser to an IV pole.
Figure 1H:
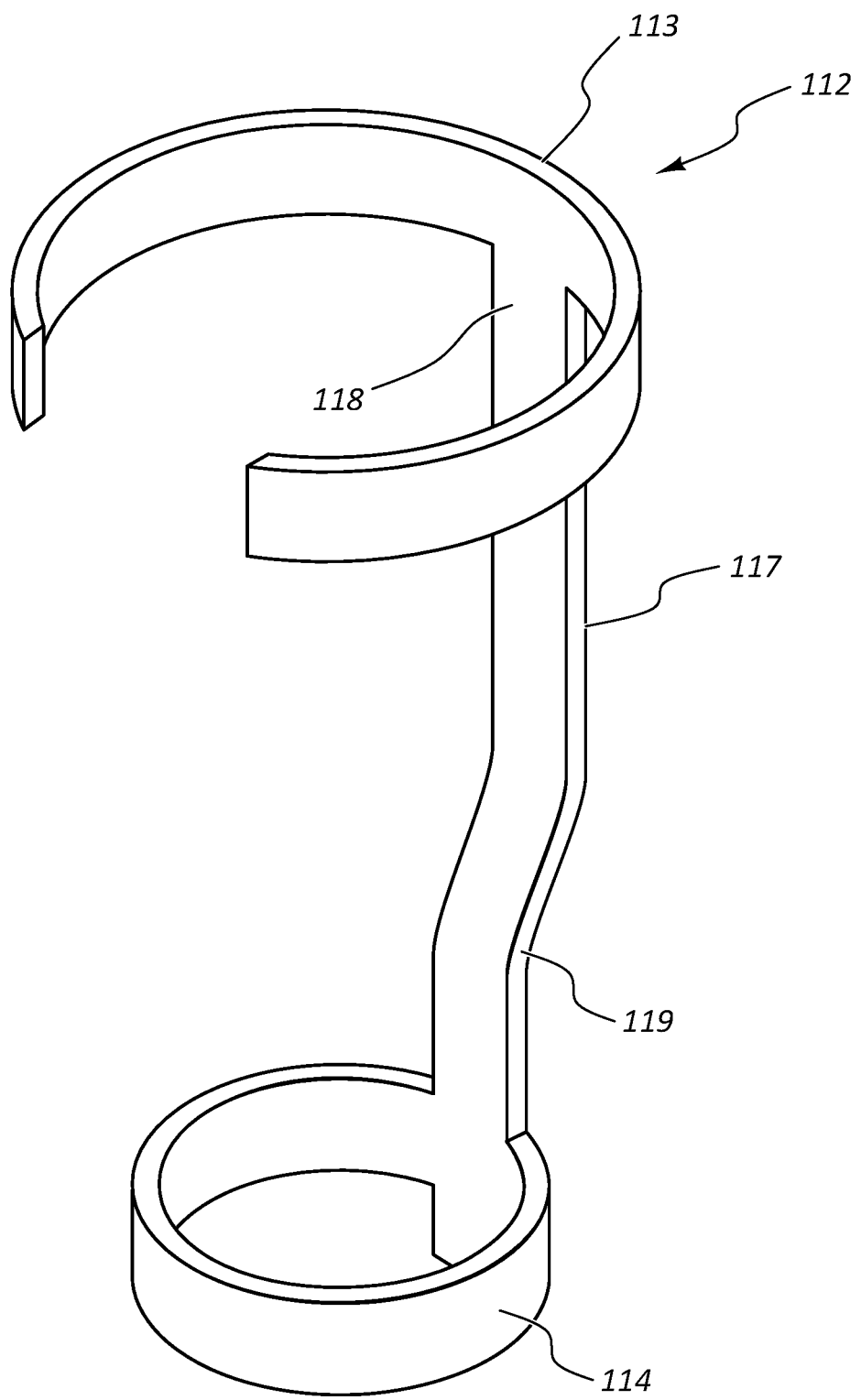
FIG. 1H is a view of ring holder for the medical device dispenser
Figure 1I:
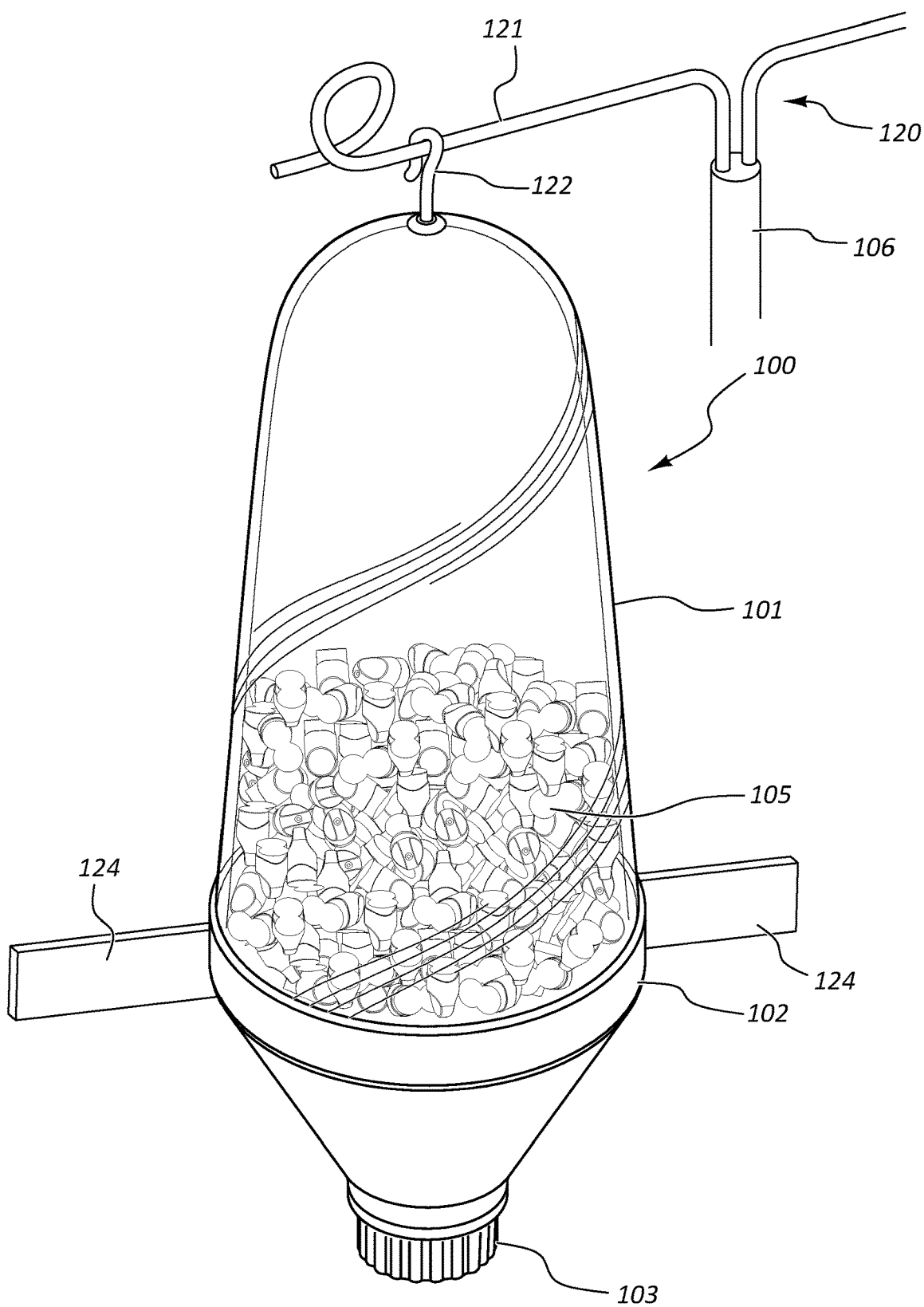
FIG. 1I is a view of the medical device dispenser coupled to the IV pole with an eye bolt.
Figure 1J:
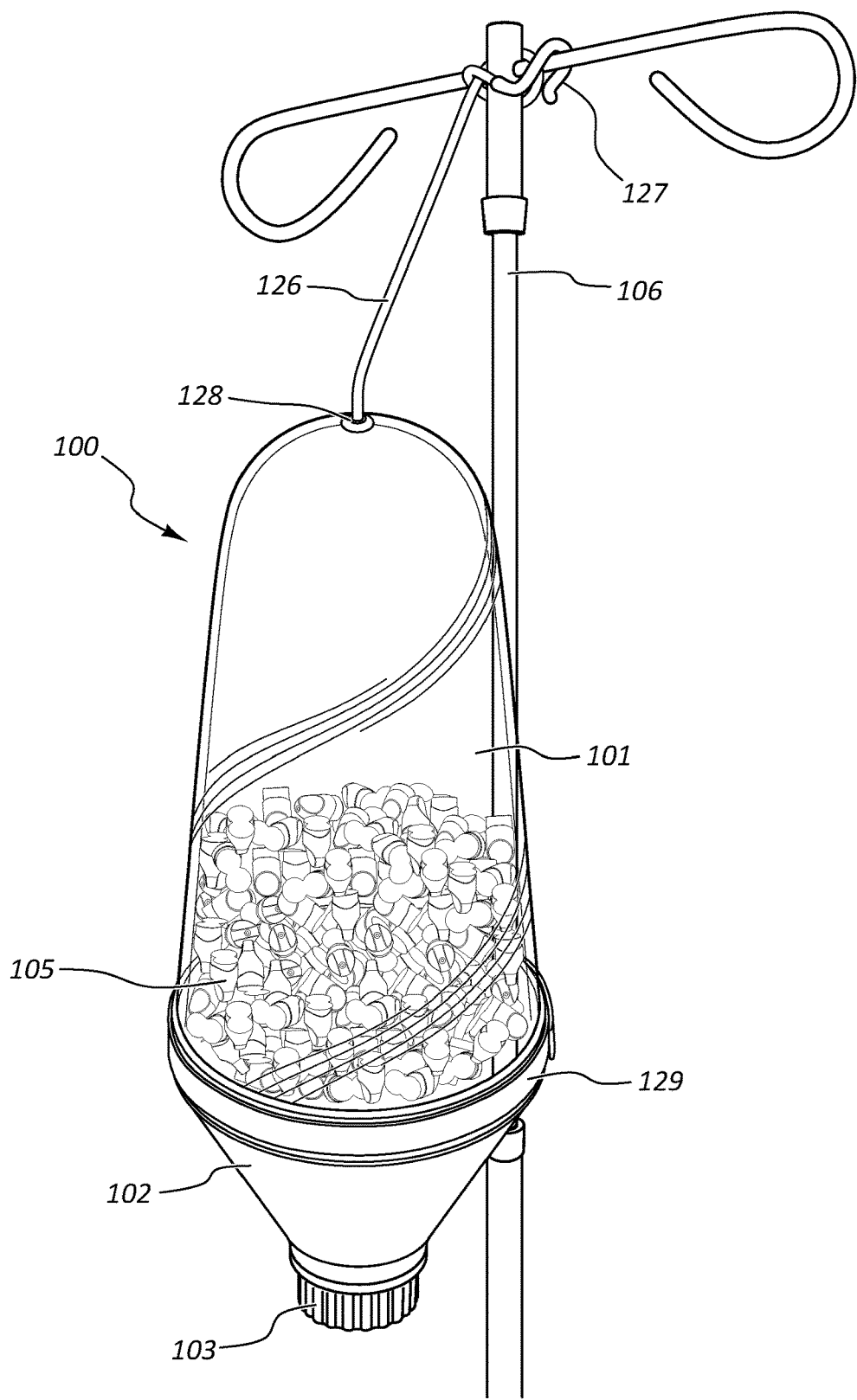
FIG. 1J is a view of the medical device dispenser coupled to the IV pole with a bungee cord.
Figure 1K:
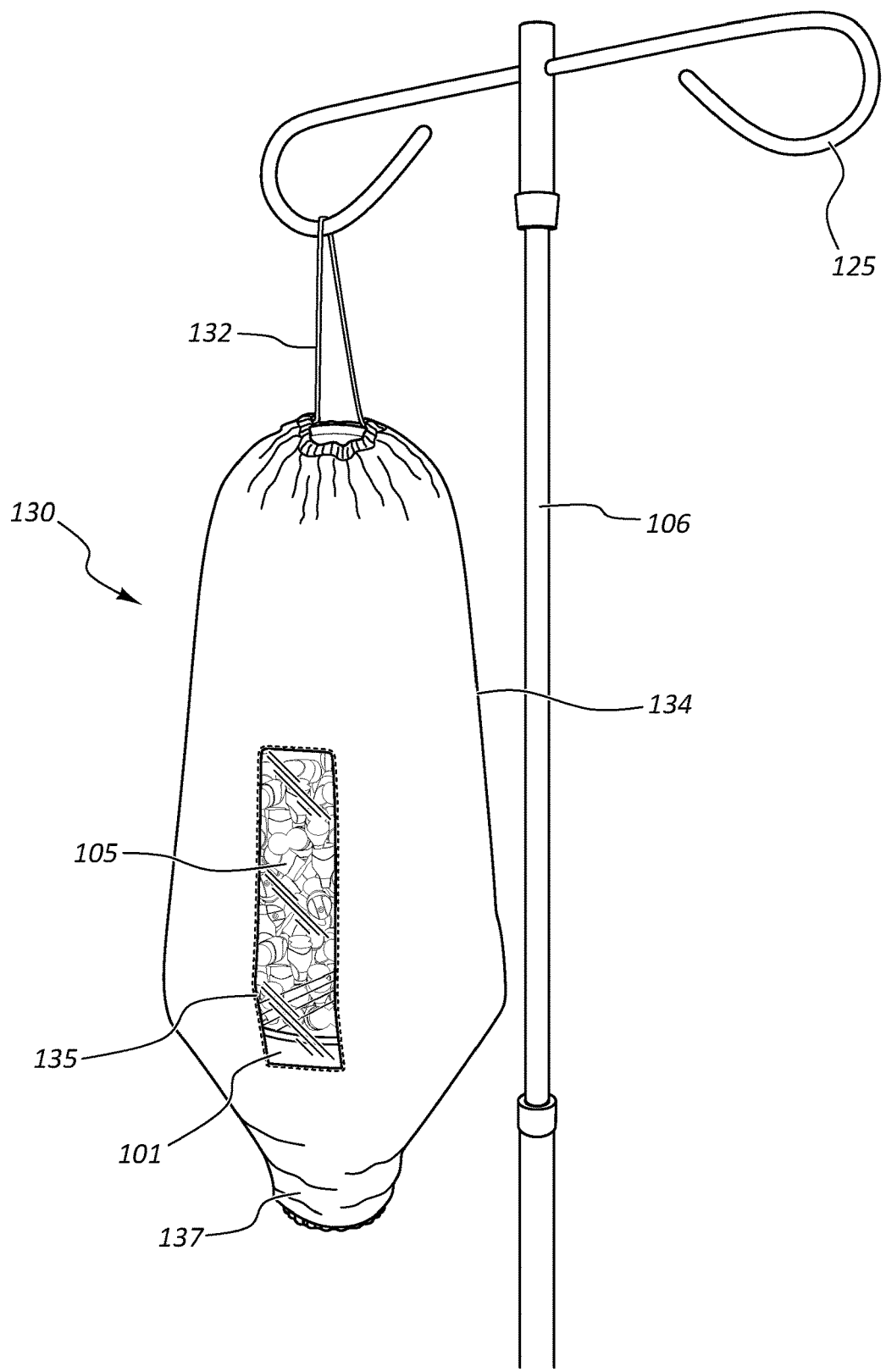
FIG. 1K is a view of the medical device dispenser coupled to the IV pole in a closable sling.
Figure 1L:
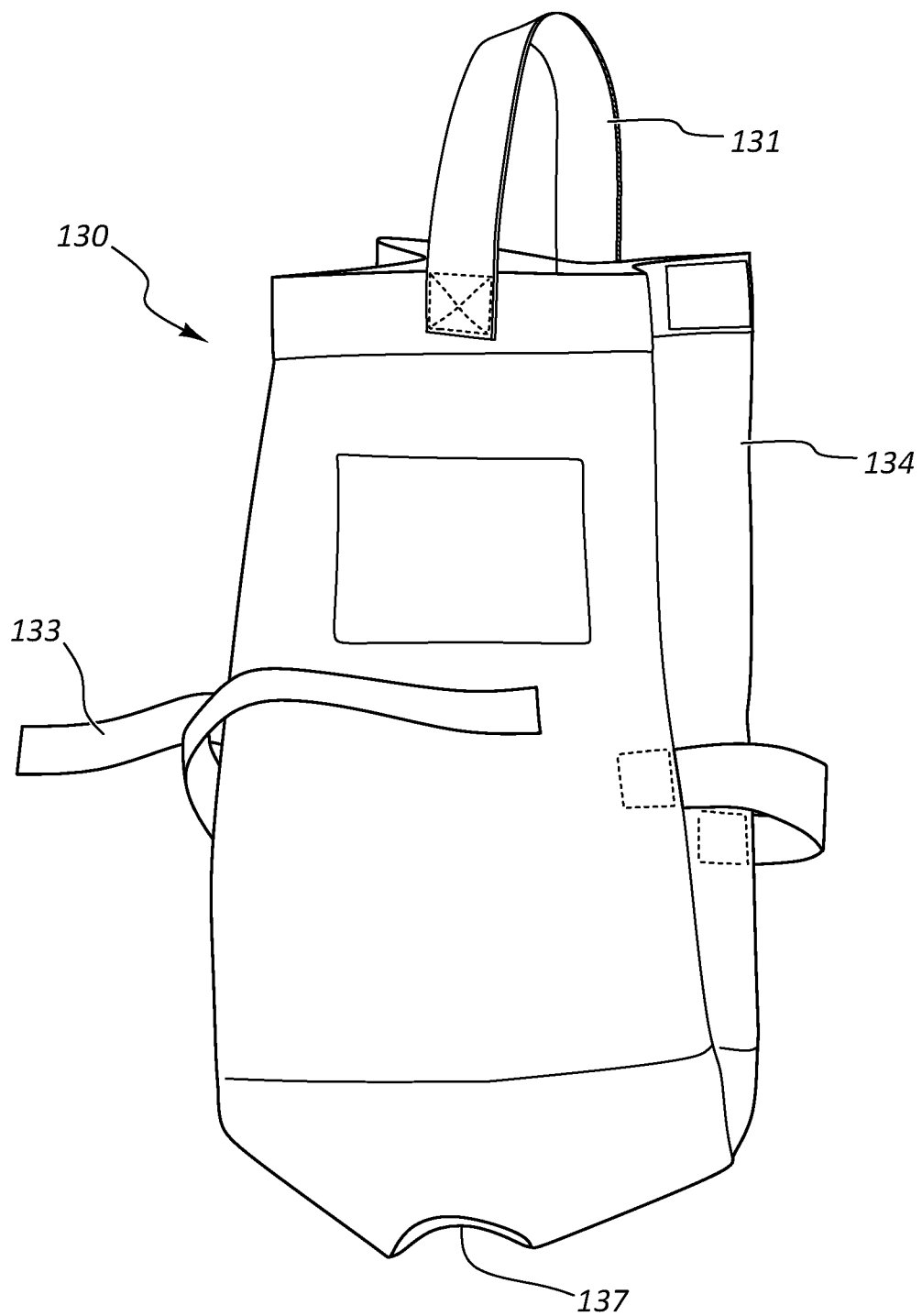
FIG. 1L is view of the medical device dispenser coupled to the IV pole in an open sling.
Figure 1M:
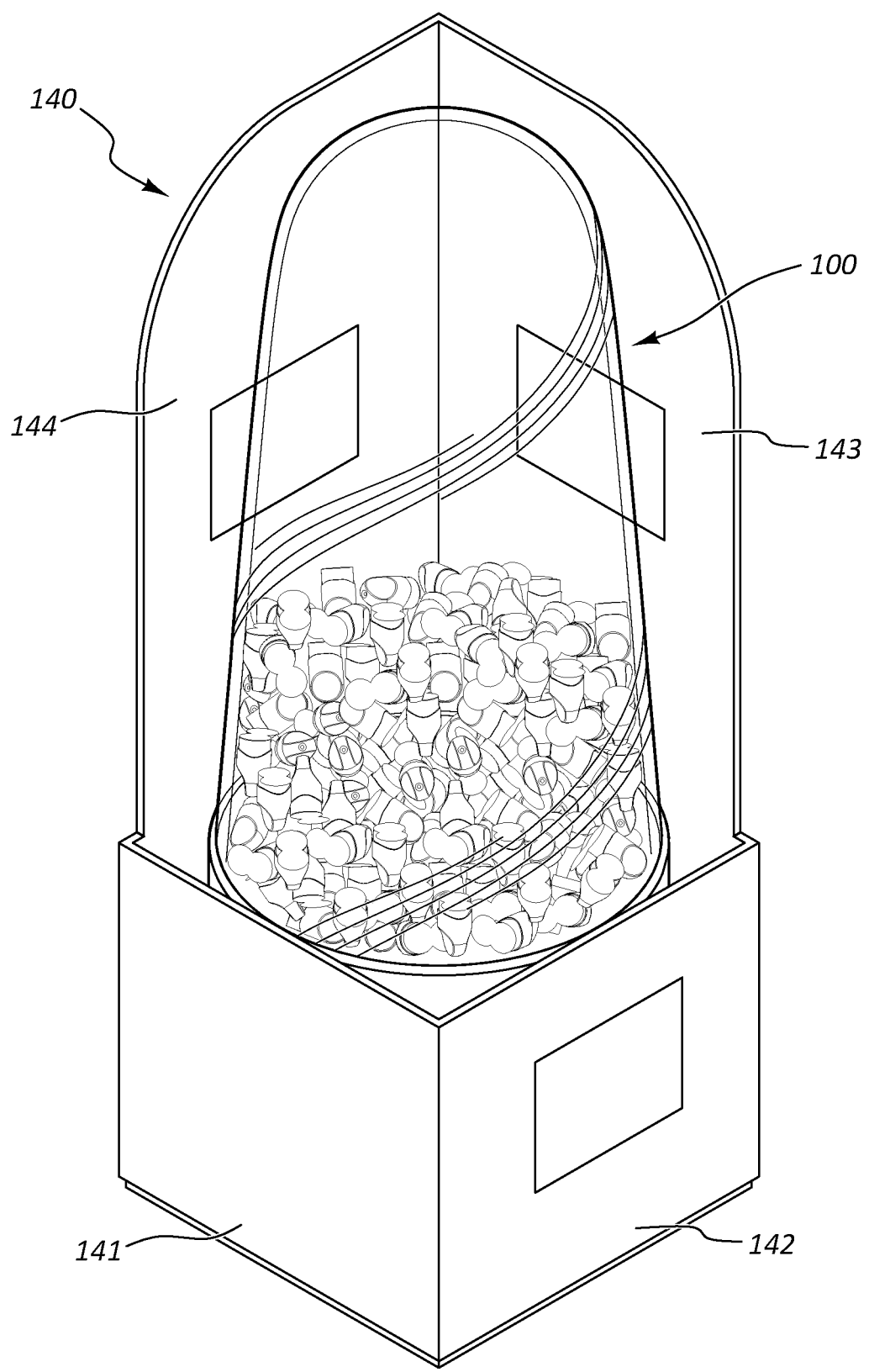
FIG. 1M is a view of a box holder holding the medical device dispenser.
Figure 1N:
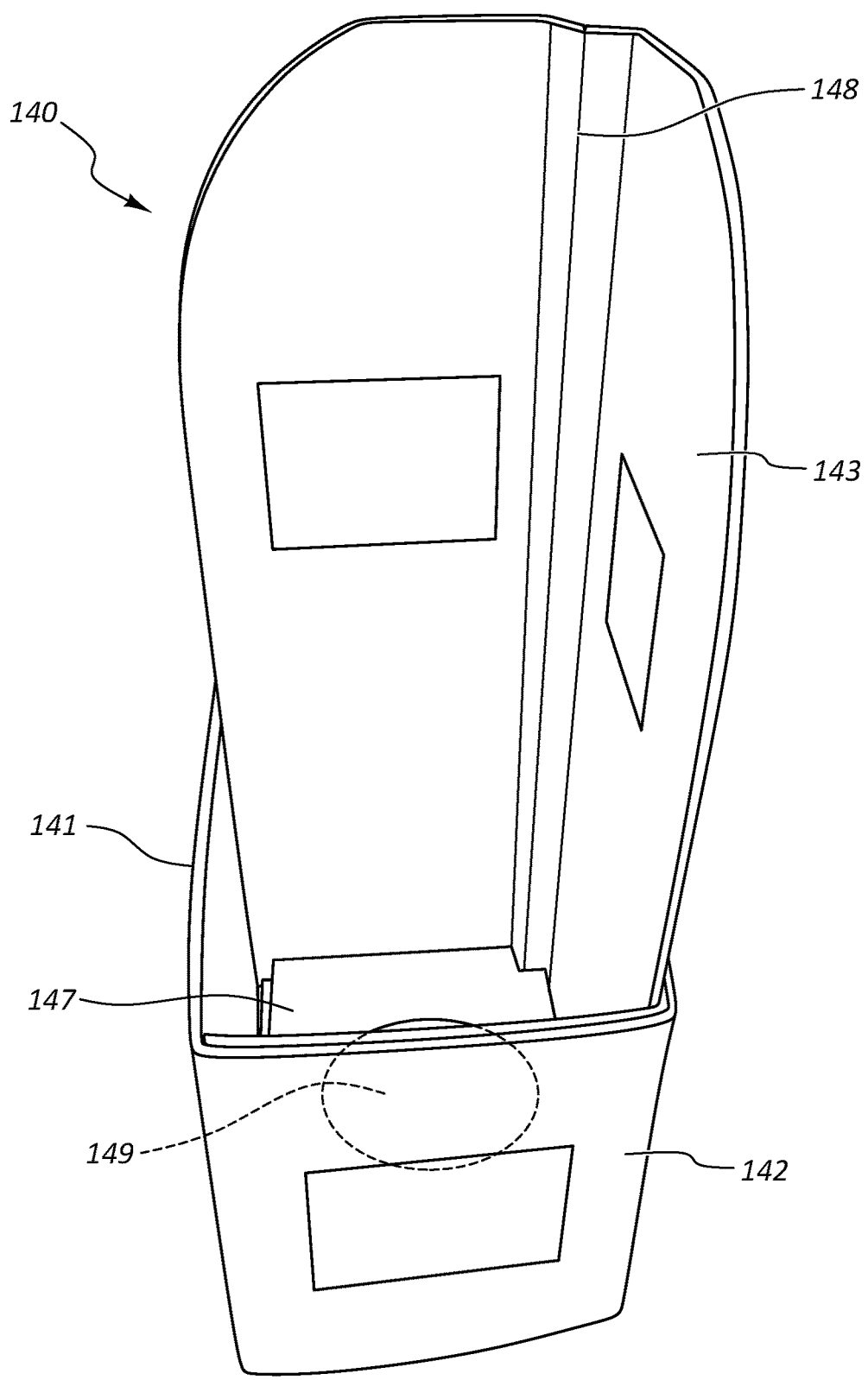
FIG. 1N is a front view of the box holder.
Figure 1O:
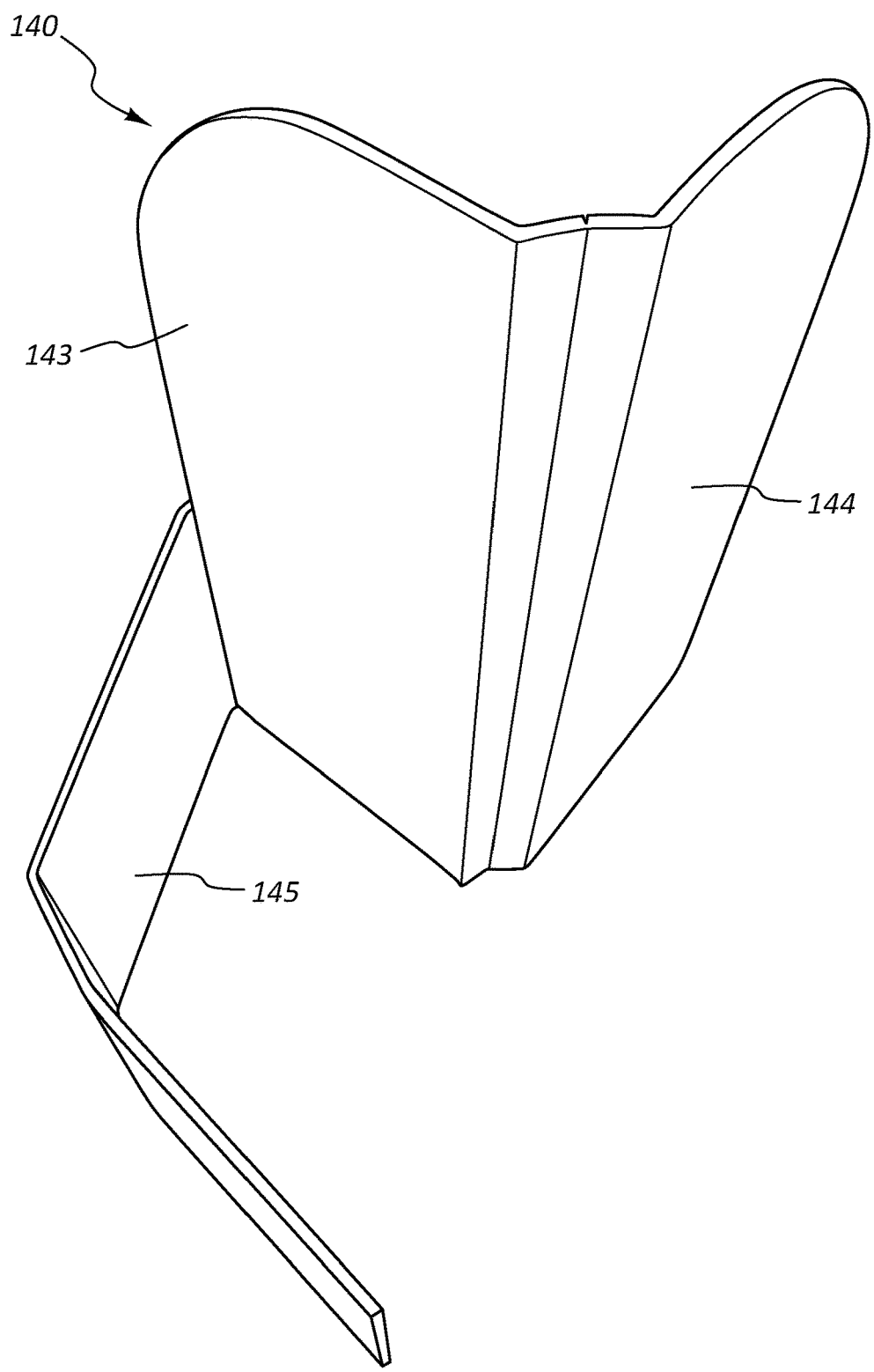
FIG. 1O is a back view of the box holder.
Figure 1P:
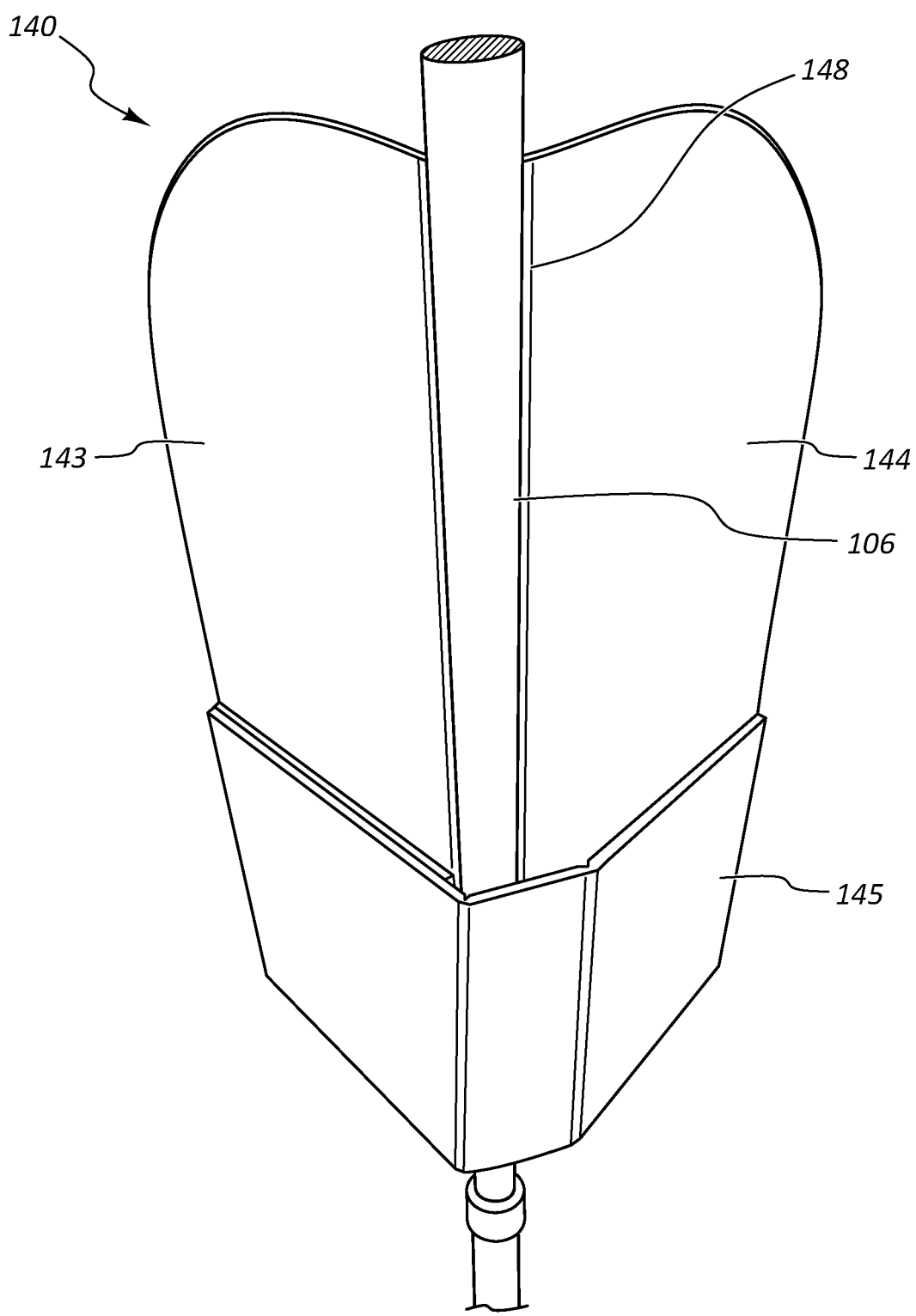
FIG. 1P is a view of the box holder coupled to the IV pole.

FIGS. 1A-1P depict an embodiment of a cap dispenser 100 and associated components utilized to couple the cap dispenser 100 to an IV pole 106. Alternatively or additionally, the cap dispenser 100 may be configured for coupling to other elements or structures. Referring to FIG. 1A, the cap dispenser 100 is composed of a hopper 101, a base 102, and a dispensing mechanism 103. The hopper 101 may be configured as a cylinder which is open at one end closed at the opposite end. The closed end may be in the shape of a dome, flat, or any other suitable shape. The open end of the hopper 101 is configured to releasably couple to the base 102. The open end and the base 102 may be configured with mating threads, a bayonet type locking mechanism, or any other suitable type of releasable coupling mechanism such that the cap dispenser 100 can be refilled with caps 105 when depleted. The cap dispenser 100 may be refilled with caps 105 by removing the hopper 101 from the base 102, filling the hopper with caps 105, and re-attaching the hopper 101 to the base 102.

In some embodiments, the hopper 101 may comprise an lockable lid 160 as shown in FIG. 1B. The lid 160 may comprise a slide 161, a capture 162, and a hinge 163. The lid 160 may be configured to be locked in a closed configuration such that a portion of the slide 161 is disposed within the capture 162. The lid 160 may be configured to open when the slide 161 is displaced from the capture 162 and the lid 160 pivots around the hinge 163. The lid 160 is configured to provide easy access to refill the cap dispenser 100 with caps 105 when the cap dispenser 100 is depleted while inhibiting unintended access to the caps 105 within the cap dispenser 100.

In some embodiments, the hopper 101 may comprise a rotatable lid 170. The rotatable lid 170 may comprise a collar 171 and a lid portion 172. The collar is configured as a ring and is coupled to an upper end of the hopper 101. The lid portion 172 is configured to be threadably coupled to the collar 171. In some embodiments, the mating threads of the collar 171 and the lid portion 172 are configured such that a 360 degree rotation of the lid portion 172 is required to remove and replace the lid portion 172. In some embodiments, the collar 171 and lid portion 172 are configured with a bayonet type of threadable coupling such that an eighth-turn or quarter-turn of the lid portion is needed to remove and replace the lid portion 172. The lid portion 172 may be opaque. In some embodiments, the lid portion 172 may be clear or translucent such that a healthcare worker can visualize through the lid portion 172 the quantity of caps 105 contained within the hopper 101. The lid portion 172 may comprise at least 2 recesses or bosses 173 in an upper surface. The recesses or bosses 173 may be disposed 180 degrees apart. The recesses or bosses 173 are configured to accommodate fingers of a healthcare worker to facilitate rotation of the lid portion 172 during removal from and replacement of the lid portion 172 to the collar 171. The lid portion 172 may be coupled to the collar 171 with a tether such that the lid portion 172 will remain with the cap dispenser 101 and not inadvertently be dropped on the floor or misplaced by the healthcare worker. The tether may be coupled to the bottom surface of lid portion 172 and to the collar 171 using any suitable coupling technique, such as a boss, screw, adhesive, welding, etc. The tether may be formed from any suitable flexible material, such as plastic, metal, cloth, etc.

In some embodiments, the hopper 101 may be transparent such that the quantity of caps 105 contained within the cap dispenser 100 can be easily determined by a healthcare worker. In some embodiments, the hopper 101 may be translucent or opaque to at least partially obscure visualization of the caps 105 by a patient to help prevent the patient from obtaining and accidentally ingesting the cap 105. A transparent window may be disposed within the translucent or opaque hopper 101, such that a healthcare worker can determine the quantity of caps 105 within the cap dispenser 100.

In some embodiments (not shown), the cap dispenser 100 may comprise a mechanism to indicate the quantity of caps 105 within the cap dispenser 100, such that a healthcare worker may be alerted as to the appropriate time the cap dispenser 100 should be refilled. The mechanism may include a plate disposed on top of the caps 105 within the hopper 101. A gauge rod can extend vertically upward from the plate and pass through the closed end of the hopper 101. The gauge rod can be marked in percentage full, fraction full, number of caps 105 remaining, or any other suitable manner to indicate the quantity of caps 105 within the cap dispenser 100. In some embodiments, the quantity of caps 105 within the cap dispenser 100 may be measured and communicated by any suitable means, such as electronically, LED display, mechanically, etc. A low volume alarm to alert the healthcare worker of a need to reload the cap dispenser 100 may be communicated using any suitable means, such as audible alarm, LED color change, flashing LED, wireless communication to remote device, etc.

The base 102 can be in the shape of a truncated hollow cone such that a cap 105 enters the base 102 at its wide end from the hopper 101 and is dispensed from a narrow end of the base 102. Other suitable shapes are also contemplated. The base 102 can be opaque. As stated above, the base 102 is configured to releasably couple to the hopper 101. The dispensing mechanism 103 is disposed at least partially within the base 102. The dispensing mechanism 103 can be configured to dispense the caps 105 one at a time using any suitable mechanism, such as rotating hole plate, nested plate, trap door, etc. The dispensing mechanism 103 may be driven by a motor coupled to a battery and a sensor to activate the motor.

In some embodiments, the dispensing mechanism 103 can comprise a horizontal roller 165 having a cap recess 166 as shown in FIG. 1D. The horizontal roller 165 may be disposed at the lower end of the base 102 such that upon horizontal rotation of the roller 165 a cap 105 can fall into the cap recess 166 when the cap recess 166 is oriented upwards and fall out of the nest 166 into the hand of a healthcare worker when the cap recess 166 is oriented downwards.

In some embodiments, the dispensing mechanism 103 can comprise a depressible hopper 167 as shown in FIG. 1E. The depressible hopper 167 may be configured to be pressed downward by the hand of a healthcare worker such that an opening 168 at the bottom of the depressible hopper 167 is opened and a cap 105 is dispensed from the depressible hopper 167. A spring mechanism may return the depressible hopper 167 to a non-depressed configuration and close the opening 168.

In some embodiments (not shown), the dispensing mechanism 103 may comprise a laterally pivoting portion. The pivoting portion may be configured to pivot about a hinge to activate the dispensing mechanism 103 and dispense a cap 105 when the pivoting portion is pushed laterally. The dispensing mechanism 103 may be manually activated by a hand of a healthcare worker.

The dispensing mechanism 103 may be locked prior activation of the dispensing mechanism 103, such that a patient or visitor cannot gain access to the caps 105. Unlocking of the dispensing mechanism 103 may be achieved by any suitable means, such as RF chip sensor, bar code, passcode, biometrics, magnetic key card, notched key card, metal key, infrared sensor, motion sensor, wireless trigger, etc. In an alternative embodiment the dispensing mechanism 103 may comprise at least one locking tab or a compressible sleeve such that the dispensing mechanism 103 is substantially "child proof."

Referring to FIG. 1F, the cap dispenser 100 is shown to further comprise a catch tray 150. The catch tray 150 may comprise a directional chute 151 and a catch tray 152. The catch tray 150 is configured to catch a cap 105 after the cap 105 is dispensed from the cap dispenser 100 instead of the cap 105 falling into the hand of a healthcare worker. The catch tray 150 may extend from a bracket such that the chute 151 and the tray 152 extend below the dispensing mechanism 103. The chute 151 is configured to direct the cap 105 into the tray 152 after the cap 105 falls from the cap dispenser 100. The chute 151 may comprise a sloping surface and at least one channel configured to direct the cap 105 into the tray 152. The tray 152 may be configured in any suitable shape to retain the cap 105, such as bowl shape, etc.

In use, a healthcare worker may couple the cap dispenser 100 to the IV pole 106 adjacent to a bed of the patient. When a new cap 105 is needed to cover a component of an infusion therapy device, the healthcare worker may unlock and activate the cap dispenser 100 such that a cap 105 is dispensed. The cap dispenser 100 may then be either manually or automatically locked such that the patient or visitor does not have access to the caps 105.

FIGS. 1G-1P illustrate embodiments of components associated with the cap dispenser 100. The components are configured to couple the cap dispenser 100 to the IV pole 106 such that the cap dispenser 100 is conveniently located a healthcare worker. Referring to FIG. 1G, the cap dispenser 100 may be coupled to the IV pole 106 utilizing a pole clamp 107. The pole clamp 107 may comprise a C-clamp 108, a knob 109, a knob bolt 110, a bracket 111 and a bracket bolt 138. The C-clamp 108 is configured to partially surround the IV pole 106. The knob bolt 110 is threadably coupled to the C-clamp 108. The knob 109 is fixedly coupled to the knob bolt 110 such that when the knob 109 is turned by the healthcare worker, a free end of the knob bolt 110 engages with the IV pole 106 to releasably secure the pole clamp 107 to the IV pole 106. The bracket 111 is fixedly coupled to the C-clamp 108 with at least one bracket bolt 138. Alternatively, the bracket 111 can be mounted on a wall of a patient's room or outside the door of the patient's room. The bracket 111 may be configured to be releasably coupled to a mating bracket disposed on the cap dispenser 100. A tab 153 may be configured to releasably couple the cap dispenser 100 to the bracket 111.

In use, the healthcare worker may couple the pole clamp 107 to the IV pole 106. The C-clamp 108 is disposed partially around the IV pole 106 and the healthcare worker turns the knob 109 to rotate the knob bolt 110 such that the free end of the bolt 110 engages the IV pole 106. The healthcare worker then couples the cap dispenser 100 to the bracket 111 of the pole clamp 107.

FIG. 1H illustrates an embodiment of a ring holder 112 configured to couple the cap dispenser 100 to the IV pole 106. The ring holder 112 may comprise an upper ring 113, a lower ring 114, and a tie bar 117. The upper ring 113 may be a complete ring or may be a C-shaped ring. The upper ring 113 may be made from a semi-flexible material such that the arms of the C-shaped ring are capable of flexing outward such that the hopper 101 of the cap dispenser 100 can laterally pass into or out of the upper ring 113. The upper ring 113 has an inside diameter sized to surround the hopper 101 of the cap dispenser 100. The upper ring 113 is fixedly coupled to an upper portion 118 of the tie bar 117 which is vertically oriented. The lower ring 114 is configured as a complete ring. The inside diameter of the lower ring 114 is sized to surround a dispensing end of the base 102 of the cap dispenser 100. The lower ring 114 is configured to support a tapered portion of the base 102. The lower ring 114 is fixedly coupled to a lower portion 119 of the tie bar 117. The upper ring 113 and the lower ring 114 are configured to function together to hold the cap dispenser 100 in an upright configuration.

In some embodiments, the lower portion 119 of the tie bar 117 may be offset from the upper portion 118 such that the central axis of the upper ring 113 is vertically aligned with the central axis of the lower ring 114. The lower portion 119 of the tie bar 117 may comprise at least one bend away from the longitudinal axis of the tie bar 117 such that the central axes of the upper ring 113 and the lower ring 114 are vertically aligned. The tie bar 117 may be fixedly or releasably coupled to a bracket coupled to an IV pole clamp. The bracket may be fixedly or releasably mounted on the wall of the patient's room or outside the door of the patient's room.

In use, a healthcare worker can couple the ring holder 112 to the IV pole 106 at a desired height utilizing the clamp. The healthcare worker can then dispose the cap dispenser 100 within the ring holder 112 by downwardly passing the cap dispenser 100 through the upper ring 113 and the lower ring 114 such that the upper ring 113 at least partially surrounds the hopper 101 of the cap dispenser 100 and the base 102 rests on the lower ring 114.

Referring now to FIG. 1I, another embodiment of the cap dispenser 100 is illustrated wherein the cap dispenser 100 comprises an eyebolt 120. The eyebolt 120 may comprise a vertically oriented ring 122 and a rod 123. The ring 122 may be fixedly coupled to the rod 123. The rod 123 may be threaded. The eyebolt 120 is fixedly coupled to the closed end of the hopper 101 of the cap dispenser 100. The rod 123 may be disposed through a hole in the hopper 101. The eyebolt 120 may be coupled to the hopper 101 using any suitable manner, such as nut and washer, adhesive, over molding, welding, etc. The cap dispenser 100 of FIG. 1I may further comprise straps 124 coupled to the cap dispenser 100. The straps 124 may be configured to couple the cap dispenser 100 to the IV pole 106 such that swinging of the cap dispenser 100 is restricted. The straps 124 may be configured from any suitable material, such as hook-and-loop material, adhesive, buckle, button, snap, etc.

In use, a healthcare worker may couple the cap dispenser 100 to the IV pole 106 utilizing the eyebolt 120. The eyebolt 120 may be directly hung from an IV bag hook 125 at the top of the IV pole 106. Alternatively, the eyebolt 120 may be hung from an S-hook 121 which hangs from the IV bag hook 125. The cap dispenser 100 may then be additionally coupled to the IV pole 106 utilizing the straps 124 to prevent swinging of the cap dispenser 100.

Referring now to FIG. 1J, the cap dispenser 100 is illustrated wherein the cap dispenser 100 comprises an elastic cord 126. The elastic cord 126 may comprise a hook 127 disposed at a first end and a knot 128 disposed at a second end. The elastic cord 126 may be coupled to the closed end of the hopper 101 of the cap dispenser 100. The second end of the elastic cord 126 may be disposed through a passage through the closed end of the hopper 101. The knot 128 may be formed in the second end such that the second end is prevented from pulling through the passage of the hopper 101. In some embodiments, a disc or sphere may be coupled to the second end or the outer diameter of the second end may be increased to prevent removal of the elastic cord 126 from the hopper 101. The cap dispenser 100 of FIG. 1J may also comprise straps 129 coupled to the cap dispenser 100. The straps 129 may be configured to couple the cap dispenser 100 to the IV pole 106 such that swinging of the cap dispenser 100 is restricted. The straps 129 may be configured from any suitable material, such as hook-and-loop material, adhesive, buckle, button, snap, etc.

In use, a healthcare worker may couple the cap dispenser 100 to the IV pole 106 utilizing the elastic cord 126. The first end of the elastic cord 126 may be looped around the top of the IV pole 106 and the hook 127 hooked around the elastic cord 126. The cap dispenser 100 may be further coupled to the IV pole 106 utilizing the straps 129 to at least partially wrap around the IV pole 106.

Referring to FIGS. 1K and 1L, the cap dispenser 100 is illustrated wherein the cap dispenser 100 is suspended from the IV pole 106 within a sling 130. The sling 130 comprises a bag 134, suspending straps 131 as shown in FIG. 1L or a draw string 132 as shown in FIG. 1K, and securement straps 133. The bag 134 may be configured to be open at its top end as illustrated in FIG. 1L. Alternatively, the bag 134 may be configured to be closable at its top end as illustrated in FIG. 1K. Any suitable manner may be used to close the bag 134, such as drawstring, hook and loop, button, snap, magnetic, releasable adhesive, etc. The bag 134 may be formed from any suitable flexible material, such as cloth, plastic, metal foil, laminates, etc. The bag 134 may comprise a transparent window 135 wherein the window 135 is configured to allow a healthcare worker to visualize the quantity of caps 105 contained within the cap dispenser 100 without removing the cap dispenser 100 from the sling 130. The bag 134 may further comprise an opening 137 in a bottom end of the bag 134. The opening 137 is configured such that a portion of the base 102 passes through the opening 137 to expose a portion of the dispensing mechanism 103. The suspending straps 131 or draw string 132 extend upwardly from the top end of the bag 134 and are fixedly coupled to the bag 134. The suspending straps 131 or draw string 132 are configured to couple to the IV bag hooks 125 of the IV pole 106 such that the sling 130 suspends from the IV bag hooks 125. The securement straps 133 may be fixedly coupled to the bag 134 and configured to extend laterally from the bag 134. The securement straps 133 are configured to be coupled to the IV pole 106 such that the sling 130 is prevented from swinging. The securement straps 133 may be formed from any suitable material, such as hook and loop, adhesive, buckle, button, snap, etc.

In use, the healthcare worker may dispose the cap dispenser 100 within the bag 134 of the sling 130 such that a portion of the base 102 and/or dispensing mechanism 103 extends through the opening 137 in the bottom of the bag 134. The bag 134 would may then be closed if the bag 134 was configured to close at the top end. The healthcare worker may dispose the suspending straps 131 or draw string 132 over the IV bag hooks 125 of the IV pole 106 such that the sling 130 is suspended from the IV bag hooks 125. The securement straps 133 may be coupled to the IV pole 106 such that the sling 130 is prevented from swinging.

Referring now to FIGS. 1M-1P, the cap dispenser 100 is shown disposed within a box holder 140. The box holder 140 comprises a first panel 141, a second panel 142, a third panel 143, a fourth panel 144, a securement band 145, and a bottom panel 147. The box holder 140 is in the general shape of a box having four sides and a bottom. The first panel 141 is coupled to the second panel 142. The second panel 142 is coupled to the third panel 143. The third panel 143 is coupled to the fourth panel 144. The bottom panel 147 is coupled to the other panels, 141, 142, 143, 144. The first panel 141 and the second panel 142 may be shorter in height than the third panel 143 and the fourth panel 144 such that the cap dispenser 100 can be disposed into the holder 140 and can be easily visualized by a healthcare worker to determine the quantity of caps 105 within the cap dispenser 100. The third panel 143 and the fourth panel 144 may be configured with a height at least equivalent to the height of the cap dispenser 100 such that the cap dispenser 100 is constrained within the box holder 140 to prevent falling out of the box holder 140. A corner 148 at which the third panel 143 and the fourth panel 144 are coupled is configured to be partially concave toward the center of the holder 140 as seen in FIG. 1J. The corner 148 is configured to at least partially surround the IV pole 106 when the box holder 140 is coupled to the IV pole 106. The securement band 145 may be fixedly coupled to the third panel 143 and extend toward the fourth panel 144 as seen in FIG. 1J. Alternatively, the securement band 145 may be fixedly coupled to the fourth panel 144 and extend toward the third panel 143. The securement band 145 comprises a means to releasably couple the free end of the securement band 145 to the fourth panel 144. The releasable coupling means may include any suitable means, such as hook and loop, magnetic, tongue and slot, snap, etc. The bottom panel 147 has a passage 149 configured such that a portion of the base 102 and/or the dispensing mechanism 103 can be disposed through the passage 149. The box holder 140 may be formed from any suitable material, such as plastic corrugated board, corrugated cardboard, plastic sheet, cardboard, etc. The box holder 140 may be configured such that the holder 140 can be shipped in a lay flat configuration and assembled by the healthcare worker.

In use, a healthcare worker may obtain the holder 140 in a lay flat configuration and assemble the box holder 140 into a functional configuration. The box holder 140 may be coupled to the IV pole 106 by disposing the corner 148 against the IV pole 106 and wrapping the securement band 145 around the opposite side of the IV pole 106 as illustrated in FIG. 1P. The securement band 145 is then coupled to the releasable coupling means. The cap dispenser 100 is disposed into the box holder 140 such that the portion of the base 102 and/or the dispensing mechanism 103 passes through the passage 149 as seen in FIG. 1M.

Figure 2A:
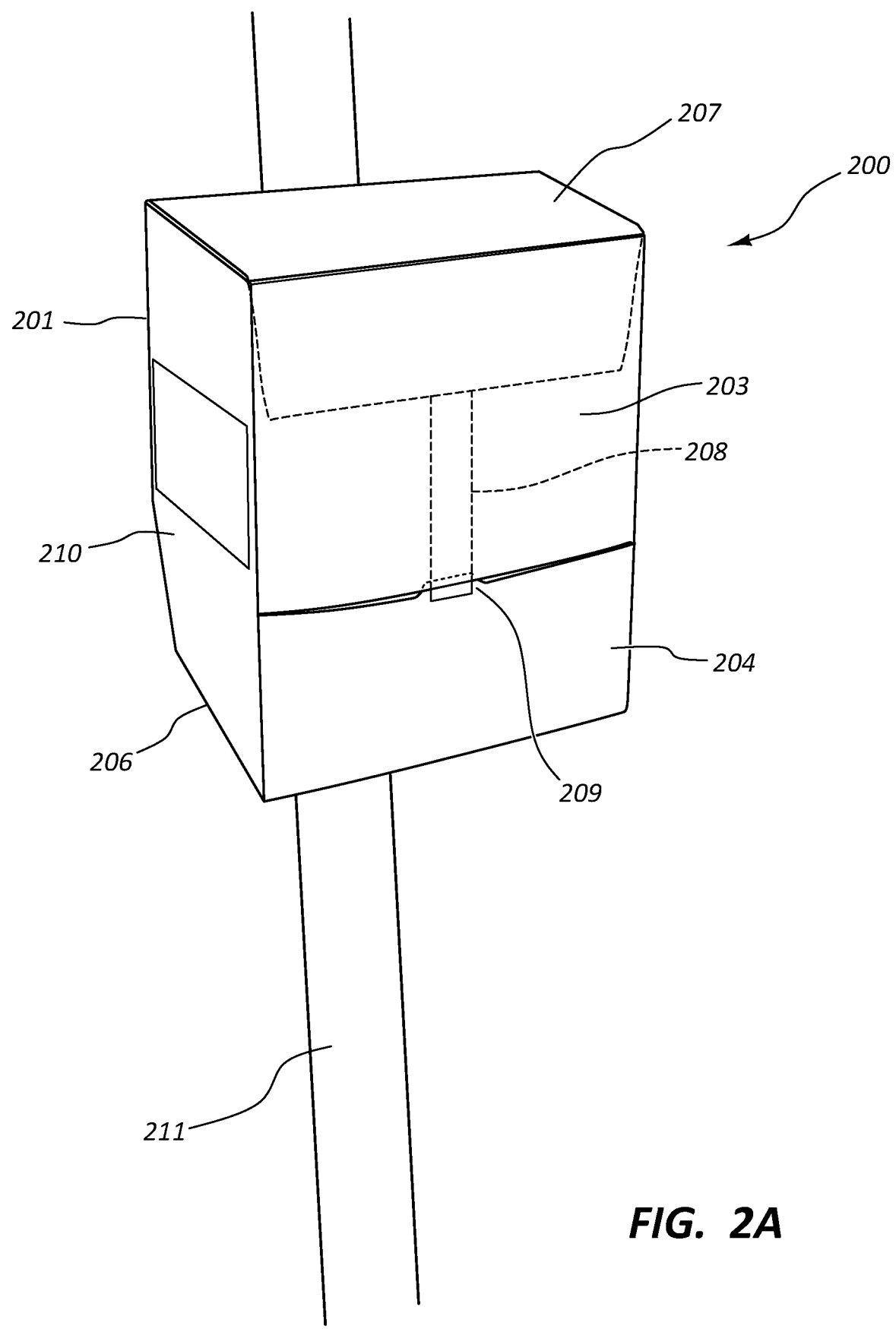
FIG. 2A is a view of a medical device dispenser box with a pivoting access in a closed configuration.
Figure 2B:
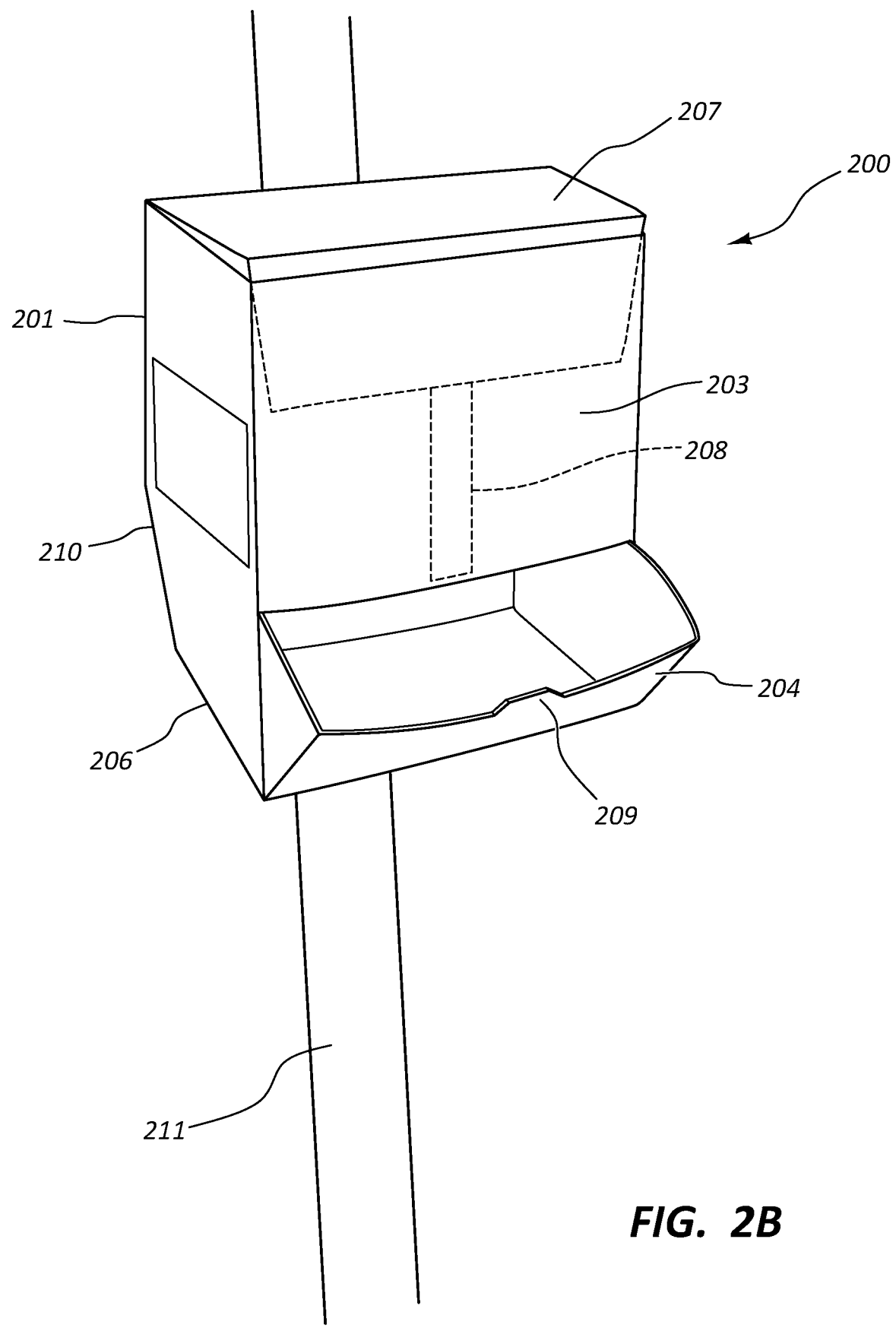
FIG. 2B is a view of the medical device dispenser box with the pivoting access in an open configuration.
Figure 2C:
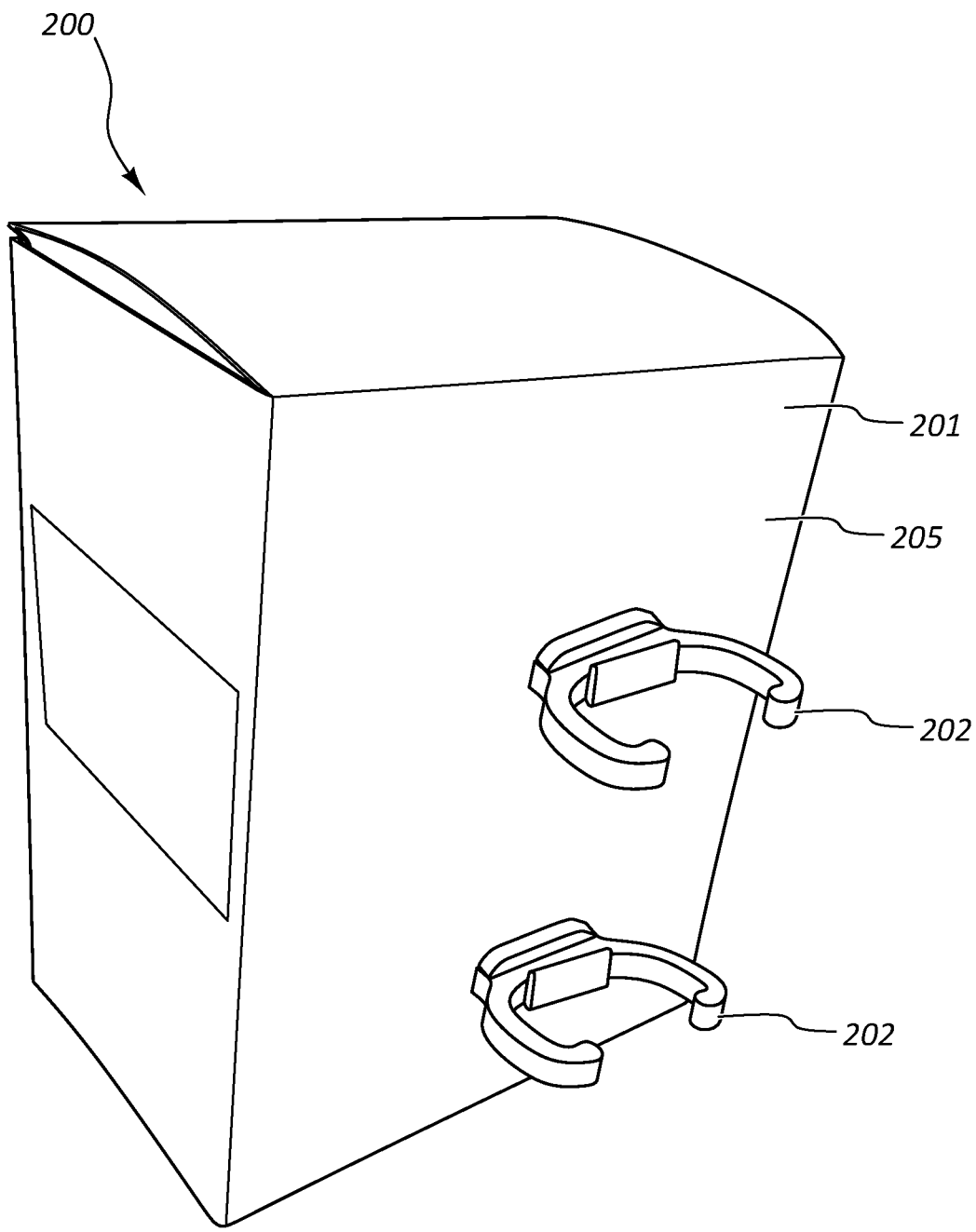
FIG. 2C is a view of the medical device dispenser box with C-clips for coupling the box to the IV pole.
Figure 2D:
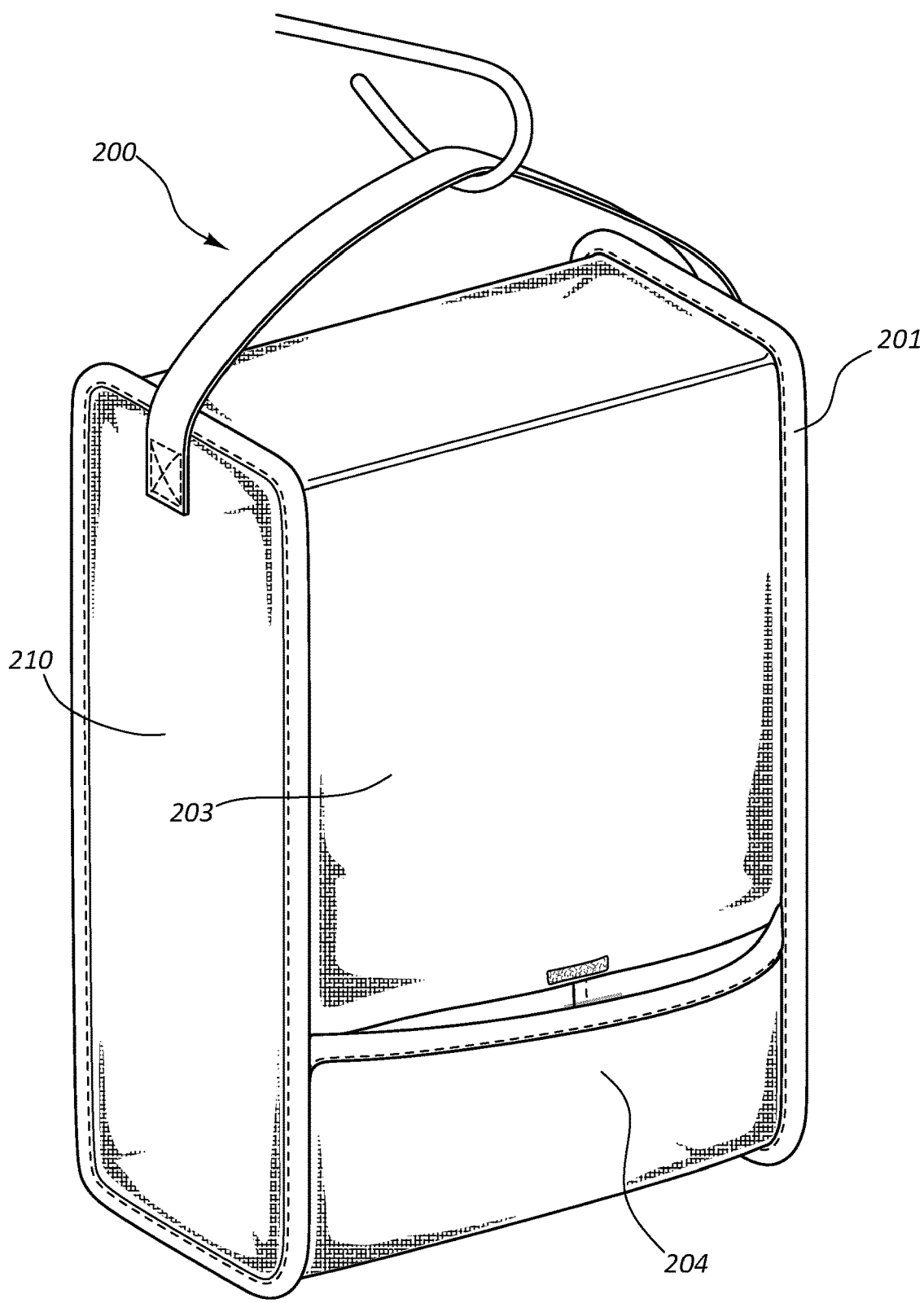
FIG. 2D is a view of a soft-sided medical device dispenser box.

Referring now to FIGS. 2A-2E, an embodiment of a cap dispenser 200 is shown. The cap dispenser 200 comprises a dispenser box 201 and clips 202. The dispenser box 201 may comprise an upper front panel 203, a lower front panel 204, a back panel 205, a bottom 206, side panels 210, a tuck lid 207, a locking tab 208 and a tab receiver 209. As shown in FIG. 2A, the dispenser box 201 is configured in a rectangular shape and is in a closed and locked configuration. The lower front panel 204 and the tuck lid 207 are closed. The locking tab 208 extends downward from the tuck lid 207 such that an end of the locking tab 208 is disposed within the tab receiver 209. FIG. 2B illustrates the dispenser box 201 in an open or dispensing configuration. The tuck lid 207 is partially lifted. The locking tab 208 is displaced from the tab receiver 209. The lower front panel 204 is pivoted open such that caps 105 may be dispensed from the cap dispenser 200. The dispenser box 201 is configured to be closed and locked by closing the lower front panel 204 and closing the tuck lid 207 such that the end of the locking tab 208 is disposed within the tab receiver 209. Alternatively, the dispenser box 201 may be locked in a closed configuration using any suitable means, such as hook and loop, adhesive, magnetic, snap, etc. The dispenser box 201 may be formed from any suitable rigid or semi-rigid material, such as plastic, chip board, etc. Alternatively, the dispenser box 201 may be formed of a flexible material such as cloth or flexible plastic as illustrated in FIG. 2D.

Referring to FIG. 2C, one or more clips 202 may be fixedly coupled to the back panel 205. The clips 202 may be configured to couple the cap dispenser 200 to an IV pole 211. The clips 202 may be configured to fold flat against the back panel 205 such that the cap dispenser 200 may be shipped to the healthcare worker in a lay flat configuration.

Figure 2E:
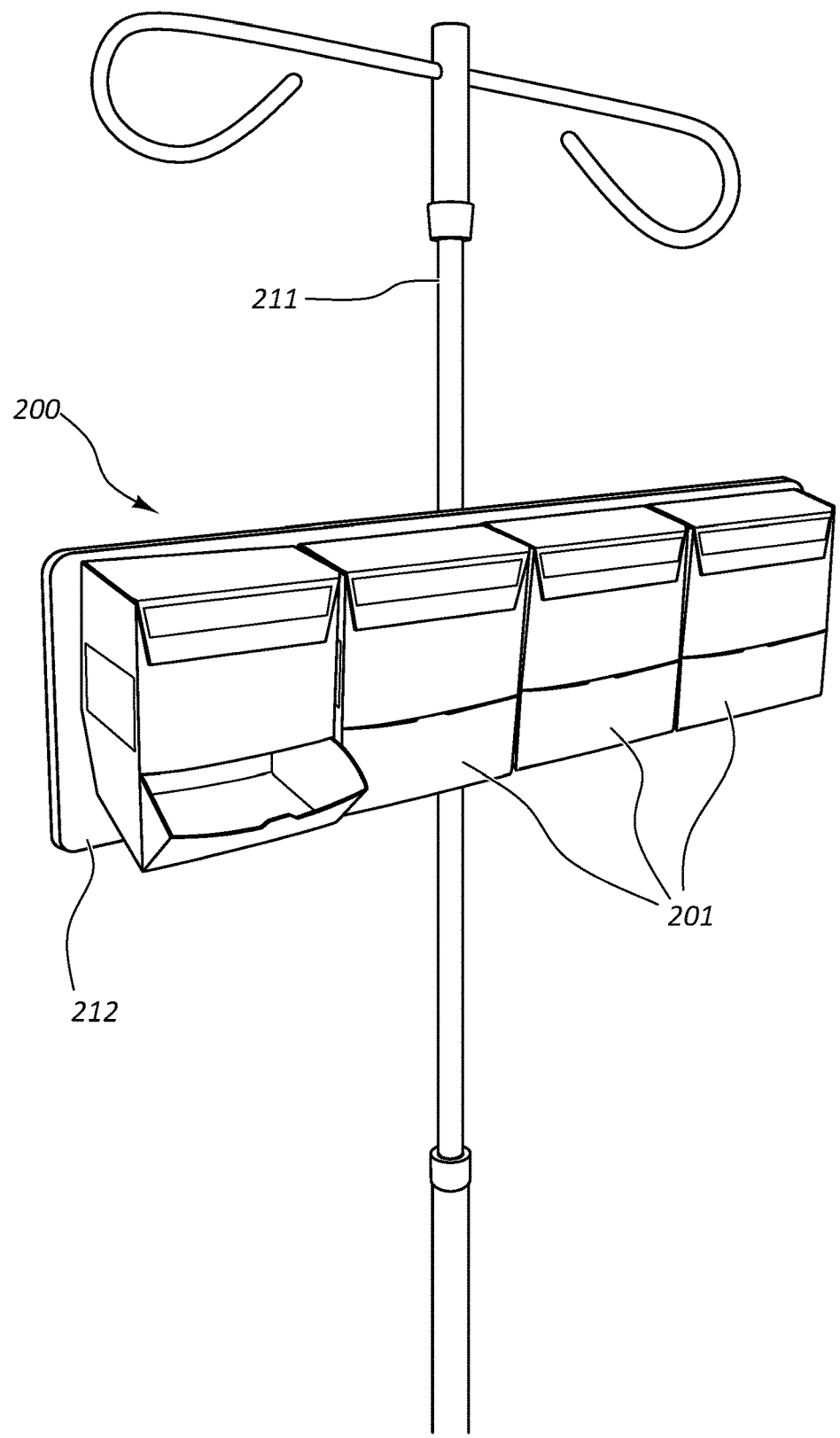
FIG. 2E is a view of the medical device dispenser box mounted on a gang bracket.

FIG. 2E illustrates yet another embodiment of cap dispenser 200. One or more dispenser boxes 201 may be coupled to a gang bracket 212 such that multiple configurations of the cap 105 may be easily accessible to a healthcare worker. The gang bracket 212 may be coupled to the IV pole 211 utilizing an IV pole clamp. In some embodiments, the gang bracket 212 may be mounted to the wall of the patient's room or outside the door of the patient's room. The gang bracket 212 may be configured as a linear bracket. In some embodiments, the gang bracket 212 may be configured with angled portions such that the gang bracket 212 partially surrounds the IV pole 211.

In use, a healthcare worker may couple the cap dispenser 200 to the IV pole 211 utilizing the clips 202. The tuck lid 207 may be partially lifted such that the end of the locking tab 208 is displaced from the tab receiver 209. The lower front panel 204 may be pivoted outward. The healthcare worker may remove at least one cap 105. The dispenser box 201 may be closed and locked by pivoting inward the lower front panel 204 and depressing the tuck lid 207 such that the locking tab 208 engages the tab receiver 209.

Without further elaboration, it is believed that one skilled in the art may use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A medical device dispenser system, comprising:
   a plurality of medical devices;
   a medical device dispenser comprising a hopper comprising an open end, a base coupled to the open end, and a dispensing mechanism; and
   a medical device dispenser holder comprising an eyebolt coupled to the hopper.

2. The medical device dispenser system of claim 1, further comprising a first panel, a second panel, a third panel, a fourth panel, and a bottom panel configured as an open box to retain the medical device dispenser.

3. The medical device dispenser system of claim 1, further comprising a catch tray.

4. The medical device dispenser system of claim 1, wherein the dispensing mechanism is activated by at least one sensor selected from a group consisting of an RFID sensor, a magnetic strip reader, a notched card key, and a metal key.

5. The medical device dispenser system of claim 1, wherein the dispensing mechanism comprises a laterally displaceable portion configured to dispense a medical device when laterally displaced.

6. The medical device dispenser system of claim 1, wherein the dispensing mechanism comprises a roller comprising a recess configured to receive the medical device.

7. The medical device dispenser system of claim 1, wherein the plurality of medical devices comprises disinfecting caps.

8. The medical device dispenser system of claim 1, wherein the hopper comprises a dome-shaped closed end.

9. The medical device dispenser system of claim 1, wherein the hopper comprises a lid.

10. The medical device dispenser system of claim 9, wherein the lid is configured to be locked in a closed configuration.

11. The medical device dispenser system of claim 9, wherein the lid is configured to be rotatably removed from the hopper.

12. A medical device dispenser system, comprising:
    a plurality of medical devices;
    a medical device dispenser comprising a hopper comprising an open end, a base coupled to the open end, and a dispensing mechanism; and
    a medical device dispenser holder comprising a first ring, a second ring, and a tie bar coupled to the first ring and the second ring, wherein the first ring is configured with a larger diameter than the second ring.

13. The medical device dispenser system of claim 12, wherein the plurality of medical devices comprises disinfecting caps.

14. The medical device dispenser system of claim 12, wherein the dispensing mechanism is activated by at least one sensor selected from a group consisting of an RFID sensor, a magnetic strip reader, a notched card key, and a metal key.

15. The medical device dispenser system of claim 12, further comprising a catch tray.

16. A medical device dispenser system, comprising:
    a plurality of medical devices;
    a medical device dispenser comprising a hopper comprising an open end, a base coupled to the open end, and a dispensing mechanism; and
    a medical device dispenser holder comprising a sling having a first opening at a first end and a second opening at a second end, suspension straps, and security straps.

17. The medical device dispenser system of claim 16, wherein the plurality of medical devices comprises disinfecting caps.

18. The medical device dispenser system of claim 16, wherein the dispensing mechanism is activated by at least one sensor selected from a group consisting of an RFID sensor, a magnetic strip reader, a notched card key, and a metal key.

19. The medical device dispenser system of claim 16, further comprising a catch tray.

20. The medical device dispenser system of claim 16, further comprising a first panel, a second panel, a third panel, a fourth panel, and a bottom panel configured as an open box to retain the medical device dispenser.

* * * * *